(12) United States Patent
Ho et al.

(10) Patent No.: US 10,807,971 B2
(45) Date of Patent: Oct. 20, 2020

(54) PYRROLIDINONE COMPOUNDS

(71) Applicant: Eli Lilly and Company, Indianapolis, IN (US)

(72) Inventors: Koc Kan Ho, Shanghai (CN); Weiguo Quan, Shanghai (CN); Jingye Zhou, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/461,475

(22) PCT Filed: Nov. 27, 2017

(86) PCT No.: PCT/US2017/063285
§ 371 (c)(1),
(2) Date: May 16, 2019

(87) PCT Pub. No.: WO2018/102256
PCT Pub. Date: Jun. 7, 2018

(65) Prior Publication Data
US 2019/0345144 A1 Nov. 14, 2019

(30) Foreign Application Priority Data
Dec. 1, 2016 (WO) ................ PCT/CN2016/108240

(51) Int. Cl.
*C07D 405/12* (2006.01)
*A61P 3/04* (2006.01)
(Continued)

(52) U.S. Cl.
CPC .............. *C07D 405/12* (2013.01); *A61P 3/04* (2018.01); *C07D 471/04* (2013.01); *A61K 45/06* (2013.01)

(58) Field of Classification Search
CPC ............................. C07D 405/12; A61K 45/06
See application file for complete search history.

(56) References Cited

U.S. PATENT DOCUMENTS 7,910,596 B2 *  3/2011  Biftu ...................... A61P 43/00
                                                    514/265.1
2010/0234403 A1    9/2010  Biftu

FOREIGN PATENT DOCUMENTS

WO    WO 2016/020031    2/2016

OTHER PUBLICATIONS

Patent Cooperation Treaty International Search Report and the Written Opinion of the International Searching Authority pertaining to International Application No. PCT/US2017/063285; dated Jan. 24, 2018.

\* cited by examiner

*Primary Examiner* — Golam M Shameem
(74) *Attorney, Agent, or Firm* — Macharri Vorndran-Jones

(57) ABSTRACT

The present invention provides compounds which are of the formula (I) and (II) wherein X is selected from the group consisting of (III) and (IV); R is selected from the group consisting of (V) and (VI); Q is selected from the group consisting of (VII) and (VIII); and (IX) R² is selected from the group consisting of (X) and (XI); or a pharmaceutically acceptable salt thereof, methods for treating obesity, type II diabetes, and compositions.

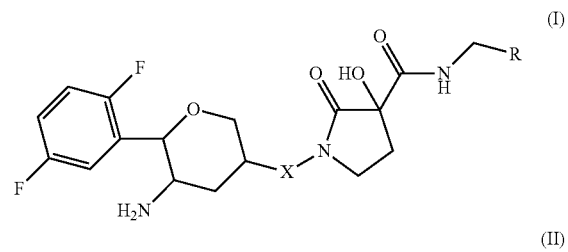

(I)

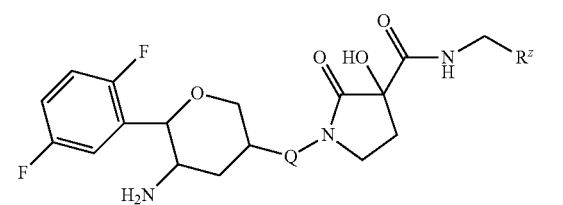

(II)

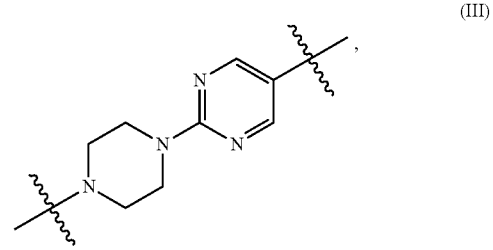

(III)

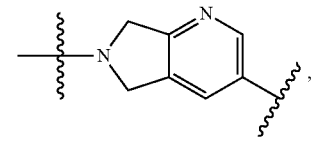

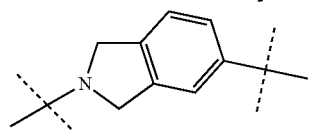

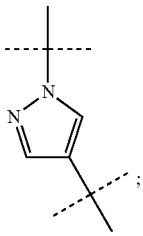

(IV)

(Continued)

-continued
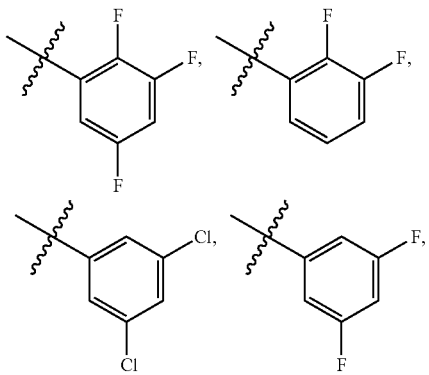 (V)
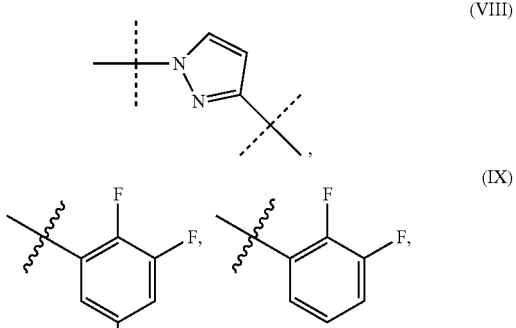 (VIII)
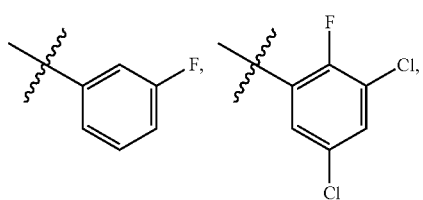 (VI)
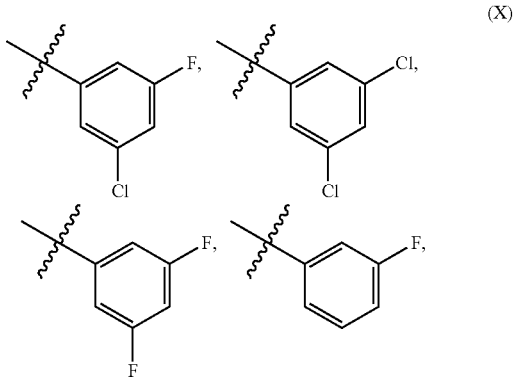 (IX)
(X)
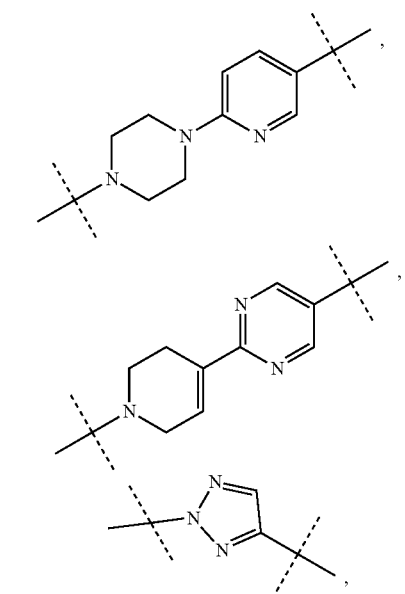 (VII)
(XI)
9 Claims, No Drawings
(51) Int. Cl.
*C07D 471/04* (2006.01)
*A61K 45/06* (2006.01)

PYRROLIDINONE COMPOUNDS

This invention relates to pyrrolidinone compounds, or pharmaceutically acceptable salt thereof, and therapeutic uses thereof. Compounds of this invention are inhibitors of methionine aminopeptidase 2 (MetAP2) and dipeptidyl peptidase-4 (DPP-4).

MetAP2 is a metalloproteinase that cleaves initiator methionine from nascent peptide emerging from the ribosomes. WO 2010/065879 reports small molecule MetAP2 inhibitors for obesity treatment.

DPP-4 inhibitors are an established drug class to improve glycemic control in patients with type 2 diabetes mellitus. Compounds with dual inhibitory activity in both MetAP2 and DPP-4 are desired.

The present invention provides novel compounds with dual MetAP2 and DPP-4 inhibition. These dual inhibitor compounds can be useful in the treatment of a MetAP2 and DPP-4 mediated condition.

The present invention provides a compound of the Formula I

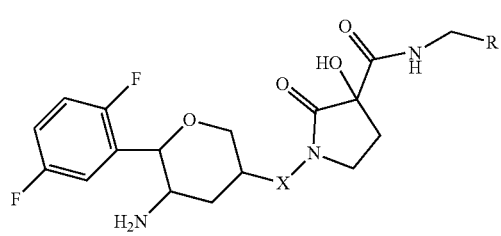

I wherein X is selected from the group consisting of

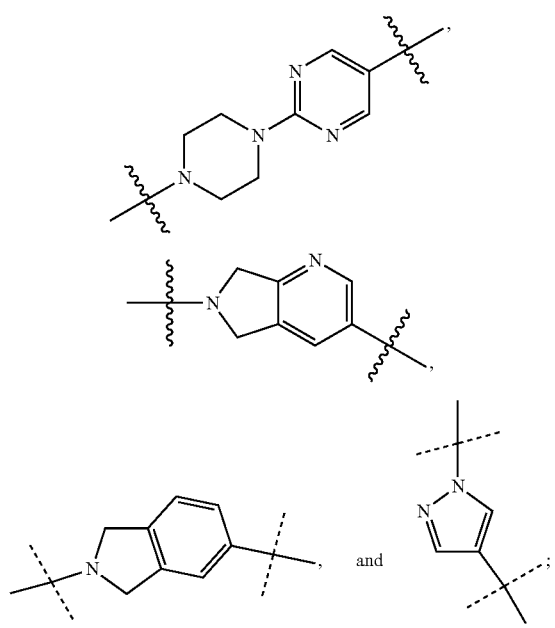

R is selected from the group consisting of

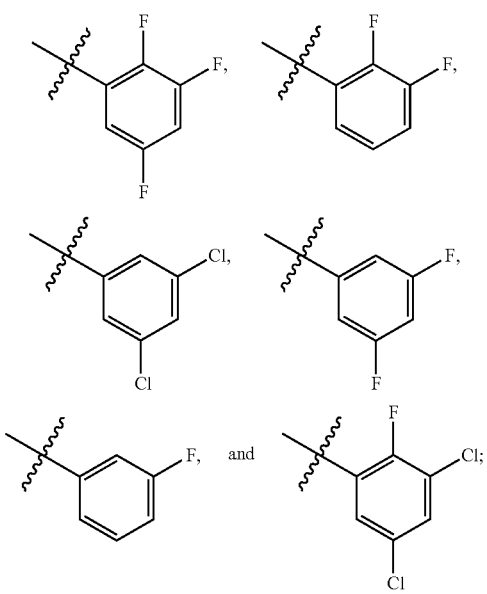

or a pharmaceutically acceptable salt thereof.

The present invention provides a compound of the Formula II

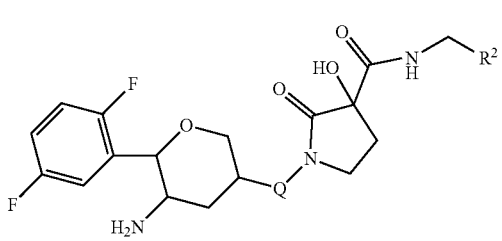

II wherein Q is selected from the group consisting of

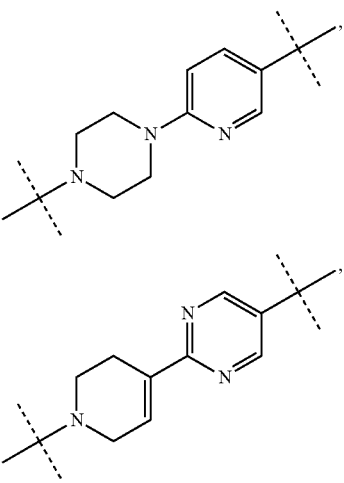

-continued and

R² is selected from the group consisting of

[structures: 2,3-difluoro-5-fluorophenyl; 2,3-difluorophenyl; 3,5-dichlorophenyl; 3-chloro-5-fluorophenyl; 3,5-difluorophenyl; 3-fluorophenyl; 2-fluoro-3,5-dichlorophenyl]

or a pharmaceutically acceptable salt thereof.

In an embodiment of the invention, X is

[pyrazole structure]

and R is selected from the group consisting of

[structures: 3,5-dichlorophenyl and 2-fluoro-3,5-dichlorophenyl]

or a pharmaceutically acceptable salt thereof.

In an embodiment of the invention X is

[isoindoline structure]

and R is selected from the group consisting of

[structures: 2,3-difluoro-5-fluorophenyl and 2,3-difluorophenyl]

or a pharmaceutically acceptable salt thereof.

In an embodiment of the invention X is

[piperazinyl-pyrimidine structure]

and R is selected from the group consisting of

[structures: 2,3-difluorophenyl and 2,3-difluoro-5-fluorophenyl]

or a pharmaceutically acceptable salt thereof.

In an embodiment Q is

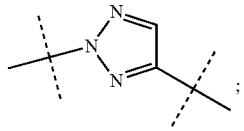

and R² is selected from the group consisting of

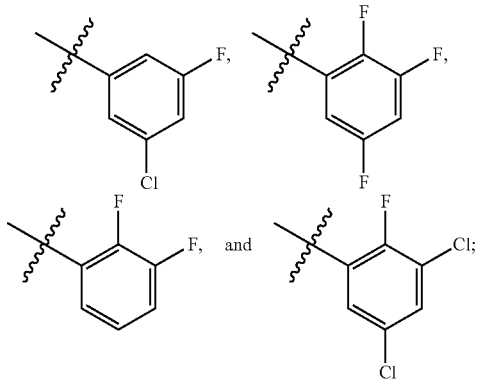

or a pharmaceutically acceptable salt thereof.

In an embodiment Q is

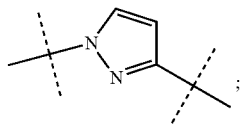

and R² is selected from the group consisting of

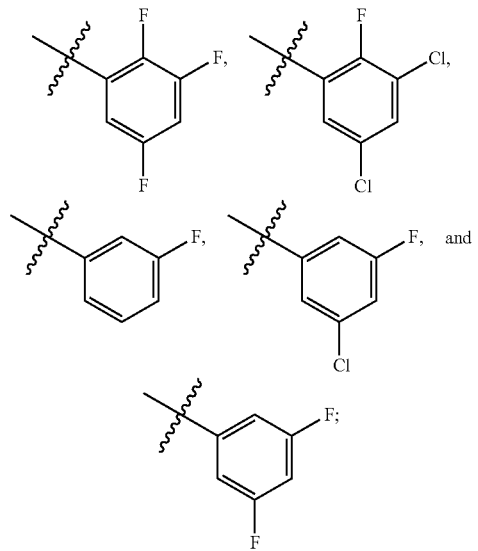

or a pharmaceutically acceptable salt thereof.

In an embodiment Q is selected from the group consisting of

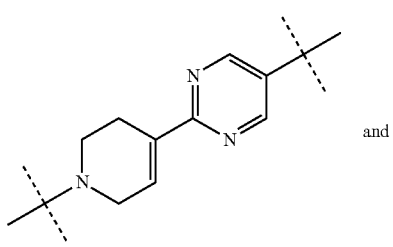

and

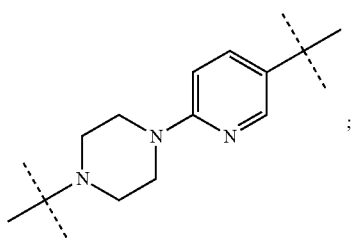

and R² is

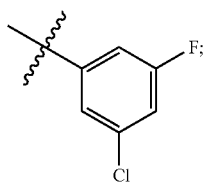 [SMILES: *c1cc(F)cc(Cl)c1]

or a pharmaceutically acceptable salt thereof.

In an embodiment Q is selected from the group consisting of

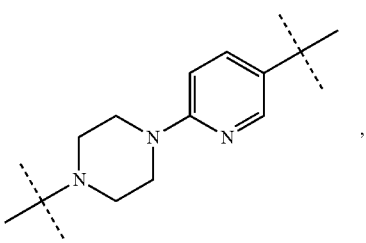

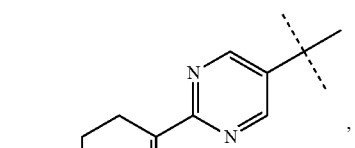

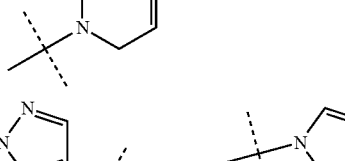

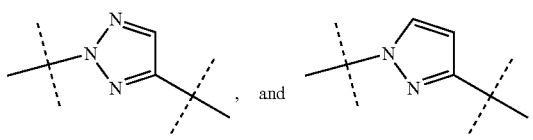

and R² is selected from the group consisting of

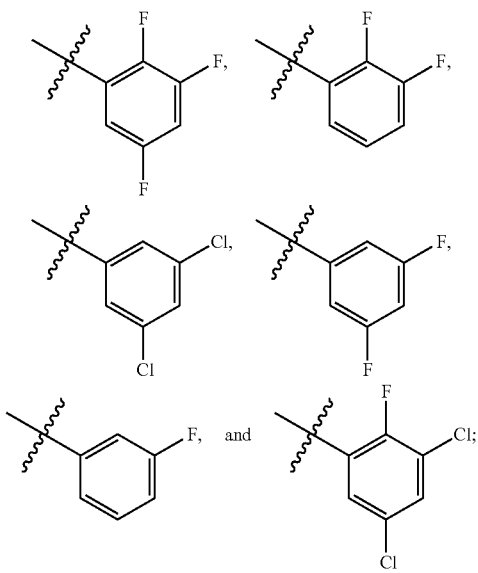

or a pharmaceutically acceptable salt thereof.

The present invention also provides a pharmaceutical composition comprising a compound of Formula I as described above or a pharmaceutically acceptable salt thereof together with one or more pharmaceutically acceptable carriers, diluents, or excipients.

The present invention also provides a method for treating obesity in a mammal. The method comprises administering to the mammal in need of treatment a compound as described above for Formula I, or a pharmaceutically acceptable salt thereof. The invention provides a method for inducing desired weight loss in a mammal in need thereof, comprising administering an effective amount of a compound of Formula I. The invention provides a method for therapeutic weight loss in a mammal in need thereof, comprising administering an effective amount of a compound of Formula I.

The present invention provides a compound according to Formula I or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of obesity in a mammal in need thereof. Preferably the mammal is a human.

The present invention also provides a pharmaceutical composition comprising a compound of Formula I as described above or a pharmaceutically acceptable salt thereof together with one or more pharmaceutically acceptable carriers, diluents, or excipients, and optionally in combination with one or more pharmaceutically active agents. Additional pharmaceutically active agents include for example, metformin and/or sitagliptin. In an embodiment of the invention the additional pharmaceutically active agent is metformin. In an embodiment of the invention the additional pharmaceutically active agent is sitagliptin. In an embodiment of the invention the additional pharmaceutically active agent is an SGLT-2 inhibitor. The skilled artisan will recognize that the second pharmaceutically active agent is suitable for administration sequentially or concomitantly with a MetAP2 modulator.

The present invention provides a method for treating a condition modulated by MetAP2 activity. The present invention provides a method for treating obesity in a patient. The invention provides a method of treating type II diabetes in a patient in need of treatment comprising administering to the patient an effective amount of a compound of Formula I or a pharmaceutically acceptable salt thereof. Preferably the patient is a human. The present invention provides a method for treating nonalcoholic steatohepatitis in a patient in need of such treatment, comprising administering to the patient an effective amount of a compound of Formula I or a pharmaceutically acceptable salt thereof.

The present invention provides use of a compound according to Formula I, or a pharmaceutically acceptable salt thereof, in the manufacture of a medicament for the treatment of obesity. The present invention provides the use of a compound according to Formula I, or a pharmaceutically acceptable salt thereof, in the manufacture of a medicament for treatment to provide therapeutic weight loss.

The present invention also provides a pharmaceutical composition comprising a compound of Formula II as described above or a pharmaceutically acceptable salt thereof together with one or more pharmaceutically acceptable carriers, diluents, or excipients.

The present invention also provides a method for treating obesity in a mammal. The method comprises administering to the mammal in need of treatment a compound as described above for Formula II, or a pharmaceutically acceptable salt thereof. The invention provides a method for inducing desired weight loss in a mammal in need thereof, comprising administering an effective amount of a compound of Formula II. The invention provides a method for therapeutic weight loss in a mammal in need thereof, comprising administering an effective amount of a compound of Formula II.

The present invention provides a compound according to Formula II or a pharmaceutically acceptable salt thereof as described above for use in therapy.

In yet another form, the present invention provides a compound as described above according to Formula II, a pharmaceutically acceptable salt thereof, or pharmaceutical composition for use in the treatment of obesity in a mammal in need thereof. Preferably the mammal is a human.

The present invention also provides a pharmaceutical composition comprising a compound of Formula II as described above or a pharmaceutically acceptable salt thereof together with one or more pharmaceutically acceptable carriers, diluents, or excipients, and optionally in combination with one or more pharmaceutically active agents. Additional pharmaceutically active agents include for example, metformin and/or sitagliptin. In an embodiment of the invention the additional pharmaceutically active agent is metformin. In an embodiment of the invention the additional pharmaceutically active agent is sitagliptin. In an embodiment of the invention the additional pharmaceutically active agent is an SGLT-2 inhibitor. The skilled artisan will recognize that the second pharmaceutically active agent is suitable for administration sequentially or concomitantly with a MetAP2 modulator.

The present invention provides a method for treating a condition modulated by MetAP2 activity. The present invention provides a method for treating obesity in a patient. The invention provides a method of treating type II diabetes in a patient in need of treatment comprising administering to the patient an effective amount of a compound of Formula II or a pharmaceutically acceptable salt thereof. Preferably the patient is a human. The present invention provides a method for treating nonalcoholic steatohepatitis in a patient in need of such treatment, comprising administering to the patient an effective amount of a compound of Formula II or a pharmaceutically acceptable salt thereof.

The present invention provides use of a compound according to Formula II, or a pharmaceutically acceptable salt thereof, in the manufacture of a medicament for the treatment of obesity. The present invention provides the use of a compound according to Formula II, or a pharmaceutically acceptable salt thereof, in the manufacture of a medicament for treatment to provide therapeutic weight loss.

The term "treating" (or "treat" or "treatment") as used herein refers to restraining, slowing, or stopping the progression or alleviating the severity of an existing symptom, condition, or disorder. It is preferable that "treating" includes alleviating symptoms in a patient with a condition associated with modulation of DPP-IV and MetAP2. Preferably "treating" includes augmenting insulin levels in a patient with type II diabetes. Preferably, "treating" includes providing therapeutic weight loss in a patient in need thereof.

As used herein, the term "effective amount" refers to the amount or dose of compound of the invention or a pharmaceutically acceptable salt thereof which upon single or multiple dose administration to the patient, provides the desired effect in the patient. Preferably, the effective amount is 500 mg or less per dose. It will be understood that the amount of active agent actually administered will be determined by a physician, in light of the relevant circumstances, including the condition to be treated, the chosen route of administration, the actual active agent administered, the age, weight, and response of the individual patient, and the severity of the patient's symptoms and other relevant circumstances.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington: The Science and Practice of Pharmacy*, L. V. Allen, Editor, 22$^{nd}$ Edition, Pharmaceutical Press, 2012.

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The abbreviations used herein are defined according to *Aldrichimica Acta*, Vol. 17, No. 1, 1984. Other abbreviations are defined as follows: "ACN" refers to acetonitrile; "AMC" refers to 7-amido-4-methylcoumarin hydrobromide; "Boc" refers to tert-butoxycarbonyl; "BSA" refers to Bovine Serum Albumin; "DCM" refers to dichloromethane; "DMF" refers to N,N-dimethylformamide; "DIO" refers to diet induced obese; "DMAc" refers to N,N-dimethylacetamide; "EDTA" refers to ethylenediaminetetraacetic acid; "Et" refers to ethyl; "EtOAc" refers to ethyl acetate; "HEC" refers to hydroxy ethyl cellulose; "HEPES" refers to 4-(2-hydroxyethyl)-1-piperazineethanesulfonic acid; "HFD" refers to high fat diet; "HOAc" refers to acetic acid; "HPLC" refers to high performance liquid chromatography; "IC$_{50}$" refers to the concentration of an agent that produces 50% of the maximal inhibitory response possible for that agent; "i-PrOH" refers to isopropanol or isopropyl alcohol; "LiHMDS" refers to lithium hexamethyldisilazide; "MeOH" refers to methanol or methyl alcohol; "R$_t$" refers to retention time; "SFC" refers to supercritical fluid chromatography; "TFA" refers to trifluoroacetic acid; "THF" refers to tetrahydrofuran, "Tris" refers to tris(hydroxymethyl)aminomethane; and "Triton™ X-100" refers to polyethylene glycol tert-octylphenyl ether.

The intermediates described in the following Schemes and preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., *Greene's Protective Group in Organic Synthesis, 5$^{th}$ Edition*, by Peter G. M Wuts, John Wiley and Sons, Inc., 2014.

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994).

The compounds of the present invention, or salts thereof, may be prepared by a variety of procedures known in the art, some of which are illustrated in the Preparations and Example below. The specific synthetic steps for each of the routes described may be combined in different ways, to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

All substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Preparation 1

N-(3-Chloro-5-fluorobenzyl)-2-oxopyrrolidine-3-carboxamide

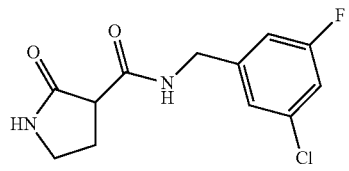 [SMILES: O=C1NCCC1C(=O)NCc1cc(F)cc(Cl)c1]

A solution of compound ethyl 2-oxopyrrolidine-3-carboxylate (180.00 g, 929.61 mmol) and (3-chloro-5-fluorophenyl) methanamine (148.36 g, 929.61 mmol) in xylene (4.00 L) is heated to 130° C. for 16 hours. LCMS showed the starting material is still present. The reaction mixture is cooled to 10° C. and a solid precipitates out after 30 minutes. The suspension is filtered and the filter cake is washed with xylene (3×500 mL), petroleum ether (2×500 mL), and dried under vacuum to give the desired product (81 g). The filtrates are concentrated under reduced pressure and the residue in xylene (3 L) is heated to 130° C. for 40 hours. The reaction mixture is cooled to 10° C. and the solid precipitates out after 30 minutes. The suspension is filtered and the filter cake is washed with xylene (2×500 mL), petroleum ether (2×500 mL) and dried in vacuum to give the title product (81.38 g) which is combined with the first lot to give a title product (164.38 g, 607.26 mmol, 65.32% yield) as a white solid. ES/MS m/z 270.9 (M+1).

Preparation 2

N-(3-Chloro-5-fluorobenzyl)-3-hydroxy-2-oxopyrrolidine-3-carboxamide

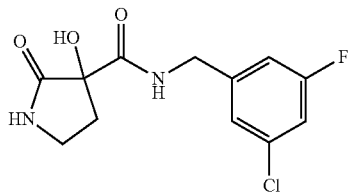 [SMILES: O=C1NCCC1(O)C(=O)NCc1cc(F)cc(Cl)c1]

N-(3-Chloro-5-fluorobenzyl)-2-oxopyrrolidine-3-carboxamide (164.38 g, 607.26 mmol) is dissolved in t-BuOH (6.00 L) at 80° C. over a period of 30 minutes. The reaction mixture is cooled to 15° C. NaOEt (206.62 g, 3.04 mol) is added and the color of solution turns to yellow from colorless. tert-Butyl hydroperoxide (626.98 mL, 4.25 mol, 65% purity) is added to the mixture at 25° C. The color of solution changes to white from yellow and a solid precipitates. The suspension is heated to 40° C. for 1 hour. The white suspension is quenched with saturated aqueous Na₂SO₃ (1500 mL) and the pH is adjusted to 7 with 4 N HCl (100 mL) and separated. The aqueous layer is extracted with DCM/i-PrOH (3/1, 2×400 mL). The combined organic extracts are concentrated under reduced pressure. The residue is dissolved in DCM/i-PrOH (3/1, 3 L) and washed with water (500 mL), brine (500 mL) and concentrated under reduced pressure. The yellow solid is slurried with DCM (400 mL) at 15° C. for 15 minutes and filtered. The filter cake is washed with DCM (3×150 mL) and dried under vacuum to give the title compound (169.00 g, 583.59 mmol, 96.10% yield) as a white solid. ES/MS m/z 286.9 (M+H).

Preparation 3

(3R)—N-[(3-Chloro-5-fluoro-phenyl)methyl]-3-hydroxy-2-oxo-pyrrolidine-3-carboxamide

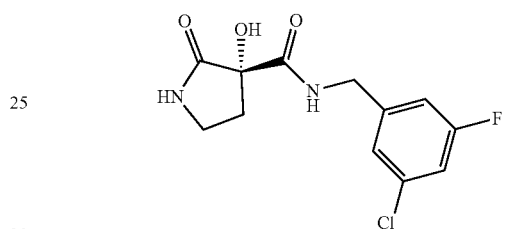

N-(3-chloro-5-fluorobenzyl)-3-hydroxy-2-oxopyrrolidine-3-carboxamide (164.00 g, 572.05 mmol) is separated by chiral SFC (instrument: SFC-7; column: AD (250 mm*50 mm, 10 μm); mobile phase: A CO₂ and B MeOH; gradient: B 45%; column temperature: 38° C.; flow rate: 200 mL/min; back pressure: 100 bar; wavelength: 220 nm) to give the title compound as the first eluting isomer (58.86 g, 205.31 mmol, 35.89% yield, $R_t$=4.45 min) as a white solid.

The following intermediates are prepared essentially by the method of (3R)—N-[(3-chloro-5-fluoro-phenyl)-3-hydroxy-2-oxo-pyrrolidine-3-carboxamide. The first eluting isomer is used for the compound preparations.

TABLE 1

| Prep No. | Chemical Name | Structure | ES/MS (m/z) (M + 1) |
|---|---|---|---|
| 4 | N-[(3,5-Dichlorophenyl)methyl]-3-hydroxy-2-oxo-pyrrolidine-3-carboxamide, isomer 1 | 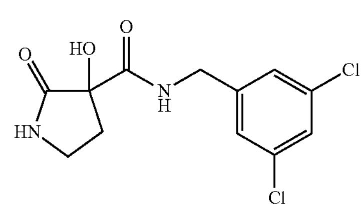 [SMILES: O=C1NCCC1(O)C(=O)NCc1cc(Cl)cc(Cl)c1] | 302.9 |
| 5 | N-[(2,3-Difluorophenyl)methyl]-3-hydroxy-2-oxo-pyrrolidine-3-carboxamide, isomer 1 | 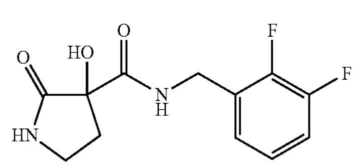 [SMILES: O=C1NCCC1(O)C(=O)NCc1cccc(F)c1F] | 270.9 |

TABLE 1-continued

| Prep No. | Chemical Name | Structure | ES/MS (m/z) (M + 1) |
|---|---|---|---|
| 6 | 3-Hydroxy-2-oxo-N-[(2,3,5-trifluorophenyl)methyl]pyrrolidine-3-carboxamide, isomer 1 | 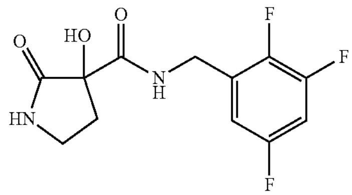 [SMILES: O=C1NCCC1(O)C(=O)NCc1cc(F)cc(F)c1F] | 288.8 |
| 7 | N-[(3-Fluorophenyl)methyl]-3-hydroxy-2-oxo-pyrrolidine-3-carboxamide, isomer 1 | 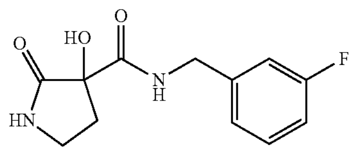 [SMILES: O=C1NCCC1(O)C(=O)NCc1cccc(F)c1] | 252.9 |
| 8 | N-[(3,5-Difluorophenyl)methyl]-3-hydroxy-2-oxo-pyrrolidine-3-carboxamide, isomer 1 | 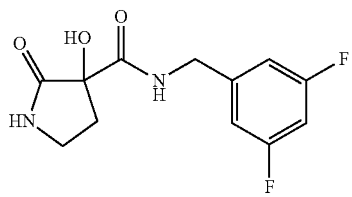 [SMILES: O=C1NCCC1(O)C(=O)NCc1cc(F)cc(F)c1] | 270.9 |
| 9 | N-[(3,5-Dichloro-2-fluoro-phenyl)methyl]-3-hydroxy-2-oxo-pyrrolidine-3-carboxamide, isomer 1 | 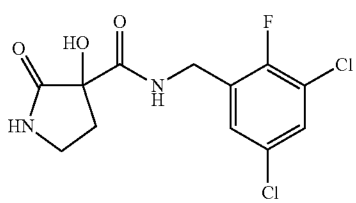 [SMILES: O=C1NCCC1(O)C(=O)NCc1cc(Cl)cc(Cl)c1F] | 320.9 |

Preparation 10 tert-Butyl 4-(5-bromopyrimidin-2-yl)-3,6-dihydro-2H-pyridine-1-carboxylate

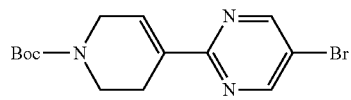

A mixture of tert-butyl 4-(4,4,5,5-tetramethyl-1,3,2-dioxaborolan-2-yl)-3,6-dihydro-2H-pyridine-1-carboxylate (22.0 g, 71.2 mmol), 5-bromo-2-iodo-pyrimidine (20.3 g, 71.2 mmol), [1,1'-bis(diphenylphosphino)ferrocene]dichloropalladium(II) (4.78 g, 6.40 mmol), sodium carbonate (22.6 g, 213 mmol) in water (80 mL) and 1,4-dioxane (400 mL) is stirred at 20° C. and purged with $N_2$ (3×). Under a $N_2$ atmosphere, the solution is heated to 90° C. and stirred for 16 hours. The suspension is concentrated to dryness and water (800 mL) is added. The mixture is extracted with EtOAc (3×500 mL). The combined organic extracts are washed with saturated brine (500 mL), dried over anhydrous sodium sulfate, filtered, and concentrated to dryness. The residue is purified by silica gel chromatography eluting with PE: EtOAc (10:1) to give the title compound (12.0 g, 70.2 mass %, 35% yield) as an off white solid. ES/MS (ESI) m/z 285.9[M+H-56]⁺.

Preparation 11

5-Bromo-2-(1,2,3,6-tetrahydropyridin-4-yl)pyrimidine

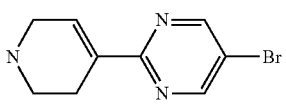

To a solution of tert-butyl 4-(5-bromopyrimidin-2-yl)-3,6-dihydro-2H-pyridine-1-carboxylate (12.0 g, 35.3 mmol) in DCM (50.0 mL) is added TFA (50.0 mL). The resulting mixture is stirred at 25° C. for 0.5 hour. To the residue is added a saturated aqueous sodium hydrogen carbonate solution (300 mL), and the mixture is extracted with EtOAc (3×200 mL). The combined extracts are washed with brine (100 mL), dried, and concentrated to give the title compound (5.84 g, 69%) as an off white solid, which is used directly without further purification. ES/MS (ESI) m/z 239.9[M+H]⁺.

Preparation 12 tert-Butyl N-[[(3R,5S,6R)-5-(tert-butoxycarbonylamino)-6-(2,5-difluorophenyl)tetrahydropyran-3-yl]amino]carbamate

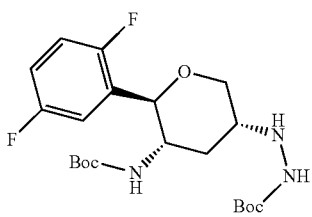 [SMILES: CC(C)(C)OC(=O)NN[C@H]1CO[C@H](c2cc(F)ccc2F)[C@@H](NC(=O)OC(C)(C)C)C1]

A solution of tert-butyl N-[(2R,3S)-2-(2,5-difluorophenyl)-5-oxo-tetrahydropyran-3-yl]carbamate (12.0 g, 36.7 mmol) and tert-butyl N-aminocarbamate (5.81 g, 44.0 mmol) in HOAc (110 mL) is stirred at 25° C. for 10 minutes. Sodium cyanoborohydride (4.85 g, 73.3 mmol) is added slowly and the mixture is stirred at 25° C. for 3 hours. The reaction mixture is diluted with water and the pH is adjusted to 9 by addition of 5 N NaOH while maintaining the reaction temperature below 20° C. The resulting suspension is filtered and the filter cake is washed with water (250 mL) and dried under vacuum. The crude product is purified by silica gel combi-flash DCM:MeOH (20:1) over 75 minutes to give the title compound as a white solid (12.5 g, 76.9%). ES/MS (m/z) 466.1 [M+Na]$^+$.

Preparation 13

(2R,3S,5R)-2-(2,5-Difluorophenyl)-5-hydrazino-tetrahydropyran-3-amine dihydrochloride

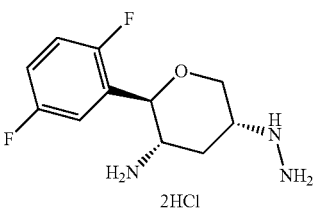 [SMILES: NN[C@H]1CO[C@H](c2cc(F)ccc2F)[C@@H](N)C1]

To a solution of tert-butyl N-[[(3R,5S,6R)-5-(tert-butoxycarbonylamino)-6-(2,5-difluorophenyl) tetrahydropyran-3-yl]amino]carbamate (12.5 g, 28.2 mmol) in DCM (100 mL) is slowly added HCl (4 mol/L) in EtOAc (90.0 mL). The resulting mixture is stirred at 16° C. for 2 hours. The solvent is evaporated under reduced pressure to give the title compound (8.50 g, 95.4%) as a white solid.

Preparation 14 tert-Butyl N-[(2R,3S)-2-(2,5-difluorophenyl)-5-hydroxy-tetrahydropyran-3-yl]carbamate

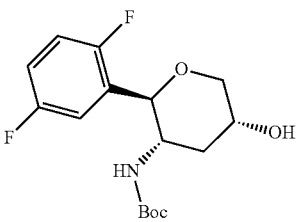 [SMILES: CC(C)(C)OC(=O)N[C@H]1C[C@@H](O)CO[C@@H]1c1cc(F)ccc1F]

Sodium borohydride (4.85 g, 128 mmol) is added slowly to a solution of O1-tert-butyl O2-methyl (2S)-4-oxopyrrolidine-1,2-dicarboxylate (14.0 g, 42.8 mmol) in ethanol (280 mL) at −20° C. The solution is stirred at −20° C. for 2 hours. The reaction mixture is adjusted to pH=6 with 1 N HCl and the mixture is extracted with DCM (3×500 ml). The combined organic extracts are washed with brine (200 ml), dried over sodium sulfate, filtered, and concentrated under reduced pressure to give the title compound (14.0 g, 93.3 mass %, 92.7% yield) as an off white solid, which is used directly without further purification. ES/MS (m/z) 273.9 [M+H−56]$^+$.

Preparation 15

[(3S,5S,6R)-5-(tert-Butoxycarbonylamino)-6-(2,5-difluorophenyl)tetrahydropyran-3-yl]4-nitrobenzoate

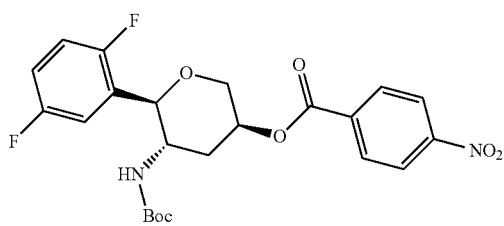 [SMILES: CC(C)(C)OC(=O)N[C@H]1C[C@H](OC(=O)c2ccc([N+](=O)[O-])cc2)CO[C@@H]1c1cc(F)ccc1F]

tert-Butyl N-[(2R,3S,5R)-2-(2,5-difluorophenyl)-5-hydroxy-tetrahydropyran-3-yl]carbamate (11.0 g, 33.4 mmol), 4-nitrobenzoic acid (27.9 g, 167 mmol), and triphenylphosphine (43.8 g, 167 mmol) are added together in THF (220 mL) and the mixture is cooled to 0° C. To the reaction mixture is slowly added diethyl azodicarboxylate (29.1 g, 167 mmol). The reaction mixture is stirred at 0° C. for 15 minutes, then warmed to 25° C. and stirred for another 16 hours. Water (500 mL) is added and the mixture is extracted with EtOAc (4×400 mL), washed with saturated brine (300 mL), dried over Na$_2$SO$_4$, and concentrated to dryness. The residue is purified by silica gel chromatography eluting with PE:EtOAc (5:1) to give the title compound (15.0 g, 71.4%) as a white solid. ES/MS (m/z) 379.0 [M+H−100]$^+$.

Preparation 16 tert-Butyl N-[(2R,3S,5S)-2-(2,5-difluorophenyl)-5-hydroxy-tetrahydropyran-3-yl]carbamate

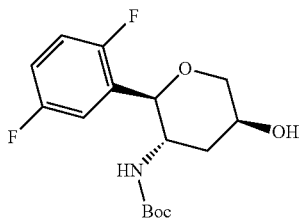 [SMILES: CC(C)(C)OC(=O)N[C@H]1C[C@H](O)CO[C@@H]1c1cc(F)ccc1F]

To a stirred solution of [(3S,5S,6R)-5-(tert-butoxycarbonylamino)-6-(2,5-difluorophenyl) tetrahydropyran-3-yl] 4-nitrobenzoate (15.0 g, 31.4 mmol) in THF (150 mL) is added a solution of lithium hydroxide (6.57 g, 157 mmol) in water (150 mL). The mixture is stirred at 25° C. for 2 hours. Water (150 mL) is added and the mixture is extracted with EtOAc (3×200 mL). The combined organic extracts are washed with saturated brine (200 ml), dried over anhydrous sodium sulfate, filtered, and concentrated. The residue is purified by silica gel flash chromatography eluting with DCM:MeOH (20:1) to give the title compound (7.00 g, 75.1 mass %, 50.9% yield) as a white solid. ES/MS (m/z) 230.0 [M+H−100]$^+$.

Preparation 17

(2R,3S,5R)-5-(4-Bromopyrazol-1-yl)-2-(2,5-difluorophenyl)tetrahydropyran-3-amine

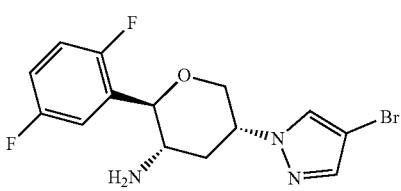 [SMILES: N[C@H]1C[C@@H](n2cc(Br)cn2)CO[C@@H]1c1cc(F)ccc1F]

To a solution of (2R,3S,5R)-2-(2,5-difluorophenyl)-5-hydrazino-tetrahydropyran-3-amine dihydrochloride (8.50 g, 26.9 mmol) and 2-bromomalonaldehyde (5.02 g, 32.3 mmol) in HOAc (170 mL) is added toluenesulfonic acid hydrate (255 mg, 1.34 mmol) and the mixture is stirred at 19° C. for 3 hours. The reaction mixture is poured into 5 N NaOH to adjust the pH to 12 and the temperature of the reaction mixture is maintained below 20° C. The mixture is extracted with DCM (3×550 mL), washed with brine, dried, and concentrated to give the title compound (6.70 g, 69.6%) as a yellow oil which is used without further purification. ES/MS (m/z) 359.9 [M+H]$^+$.

Preparation 18 tert-Butyl N-[(2R,3S,5R)-5-(4-bromopyrazol-1-yl)-2-(2,5-difluorophenyl)tetrahydropyran-3-yl]carbamate

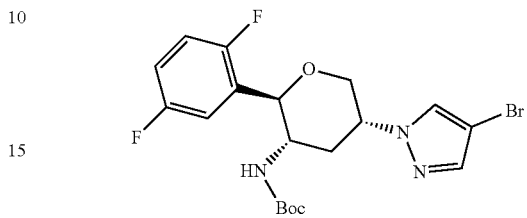

To a solution of (2R,3S,5R)-5-(4-bromopyrazol-1-yl)-2-(2,5-difluorophenyl)tetrahydropyran-3-amine (6.50 g, 18.1 mmol) and triethylamine (9.27 g, 90.7 mmol) in DCM (200 mL) is added di-tert-butyl dicarbonate (10.0 g, 45.4 mmol) and the mixture is stirred at 12° C. for 16 hours. Water (300 mL) is added and the mixture is extracted with DCM (3×300 mL), washed with 0.05 N HCl solution (100 mL) brine, dried, and concentrated to dryness. The crude product is purified by silica gel combi-flash eluting with PE:EtOAc (5:1) to give the title compound (3.70 g, 92.8 mass %, 41.3% yield) as a yellow solid. ES/MS (m/z) ($^{79}$Br/$^{81}$Br) 358.1/360.1 [M+H−100]$^+$.

Preparation 19 tert-Butyl N-[(2R,3S,5R)-5-(3-bromopyrazol-1-yl)-2-(2,5-difluorophenyl)tetrahydropyran-3-yl]carbamate

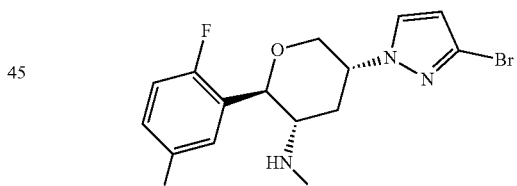

To a suspension of tert-butyl N-[(2R,3S,5S)-2-(2,5-difluorophenyl)-5-hydroxy-tetrahydropyran-3-yl]carbamate (0.500 g, 1.50 mmol), 3-bromo-1H-pyrazole (0.331 g, 2.25 mmol) and triphenylphosphine (0.591 g, 2.25 mmol) in THF (10.0 mL) is added diethyl azodicarboxylate (0.393 g, 2.25 mmol). The reaction is stirred at 25° C. for 16 hours and then concentrated to dryness. Water (50 mL) is added and the mixture is extracted with EtOAc (3×40 mL). The combined organic extracts are washed with saturated brine (40 ml), dried over anhydrous sodium sulfate, filtered, and concentrated to dryness. The residue is purified by silica gel flash chromatography eluting with PE:EtOAc (5:1) to give the title compound (0.150 g, 93.7 mass %, 20.4% yield) as a white solid, which is used without further purification. ES/MS (m/z) ($^{79}$Br/$^{81}$Br) 359.9/361.9 [M+H−100]$^+$.

Preparation 20 tert-Butyl N-[(2R,3S,5R)-5-(4-bromotriazol-2-yl)-2-(2,5-difluorophenyl)tetrahydropyran-3-yl]carbamate

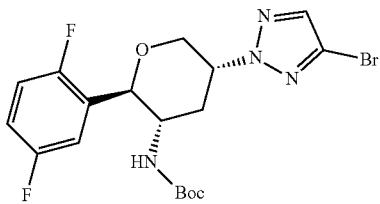 [SMILES: CC(C)(C)OC(=O)N[C@H]1C[C@@H](n2ncc(Br)n2)CO[C@@H]1c1cc(F)ccc1F]

To a suspension of tert-butyl N-[(2R,3S,5S)-2-(2,5-difluorophenyl)-5-hydroxy-tetrahydropyran-3-yl]carbamate (7.00 g, 21.3 mmol), 4-bromo-1H-triazole (3.30 g, 22.3 mmol) and triphenylphosphine (8.36 g, 31.9 mmol) in THF (140 mL) is added diethyl azodicarboxylate (5.55 g, 31.9 mmol). The reaction is stirred at 25° C. for 16 hours. The mixture is concentrated and water (400 mL) is added. The mixture is extracted with EtOAc (3×300 mL). The combined organic extracts are washed with saturated brine (300 ml), dried over anhydrous sodium sulfate, filtered, and concentrated to dryness. The residue is purified by silica gel flash chromatography eluting with PE:EtOAc (5:1) to give the title compound (2.70 g, 26.4%) as a white solid. ES/MS (m/z) ($^{79}$Br/$^{81}$Br) 359.0/361.0 [M+H−100]$^+$.

Preparation 21 tert-Butyl N-[(2R,3S,5R)-5-(5-bromoisoindolin-2-yl)-2-(2,5-difluorophenyl)tetrahydropyran-3-yl]carbamate

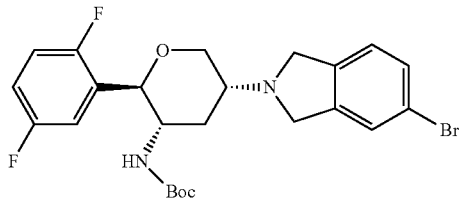 [SMILES: CC(C)(C)OC(=O)N[C@H]1C[C@@H](N2Cc3ccc(Br)cc3C2)CO[C@@H]1c1cc(F)ccc1F]

To a solution of 5-bromoisoindoline hydrochloride (3.00 g, 12.5 mmol) and tert-butyl N-[(2R,3S)-2-(2,5-difluorophenyl)-5-oxo-tetrahydropyran-3-yl]carbamate (4.14 g, 12.7 mmol) in DMAc (120 mL) is added triethylamine (3.5 mL, 25.1 mmol). The resulting mixture is stirred at 10° C. for 15 minutes. Then HOAc (2.26 g, 37.6 mmol) is added and the mixture is stirred for 1 hour. Sodium triacetoxyborohydride (10.6 g, 50.1 mmol) is added to the solution at 0° C. The resulting mixture is stirred at 10° C. for 16 hours. The pH of the reaction mixture is adjusted to 5-6 with 1 M HCl aqueous solution. The resulting solution is diluted with water (800 mL) and extracted with EtOAc (3×300 mL). The combined organic extracts are washed with brine (3×500 mL), dried over anhydrous sodium sulfate, and concentrated under reduced pressure. The crude product is purified by silica gel flash chromatography eluting with DCM:MeOH (50:1) to give the title compound (5.50 g, 84.4%) as a brown solid. ES/MS (m/z) ($^{79}$Br/$^{81}$Br) 511.4/513.4 [M+H].

Preparation 22 tert-Butyl N-[(2R,3S,5R)-2-(2,5-difluorophenyl)-5-[4-(5-iodopyrimidin-2-yl)piperazin-1-yl]tetrahydropyran-3-yl]carbamate

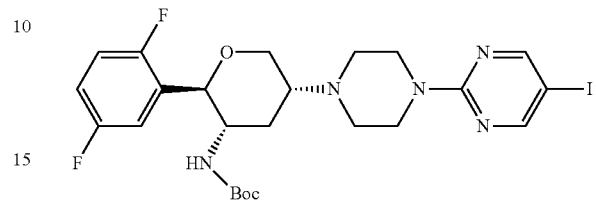

To a solution of 5-iodo-2-piperazin-1-yl-pyrimidine (10.0 g, 33.4 mmol) and tert-butyl N-[(2R,3S)-2-(2,5-difluorophenyl)-5-oxo-tetrahydropyran-3-yl]carbamate (11.5 g, 35.1 mmol) in DMAc (100 mL) is added HOAc (2.01 g, 33.4 mmol) and the mixture is stirred at 8° C. for 1 hour. Sodium triacetoxyborohydride (17.7 g, 83.6 mmol) is added to the solution at 0° C. and the resulting mixture is stirred at 8° C. for 16 hours. The reaction mixture is poured into water (500 mL). The precipitate is collected by filtration and the solid is dried under vacuum to give the crude product. The crude product is purified by silica gel flash chromatography eluting with PE:EtOAc (1:1) to give the title compound (3.80 g, 18.9%) as a white solid. ES/MS (m/z) 602.1 [M+H].

Preparation 23 tert-Butyl N-[(2R,3S,5R)-5-[4-(5-bromopyrimidin-2-yl]-3,6-dihydro-2H-pyridin-1-yl]-2-(2,5-difluorophenyl)tetrahydropyran-3-yl]carbamate

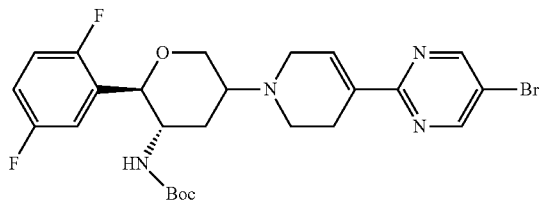 [SMILES: CC(C)(C)OC(=O)N[C@H]1CC(N2CC=C(c3ncc(Br)cn3)CC2)CO[C@@H]1c1cc(F)ccc1F]

To a suspension of 5-bromo-2-(1,2,3,6-tetrahydropyridin-4-yl)pyrimidine (5.84 g, 24.3 mmol) and tert-butyl N-[(2R,3S)-2-(2,5-difluorophenyl)-5-oxo-tetrahydropyran-3-yl]carbamate (7.96 g, 24.3 mmol) in DMAc (120 mL) is added HOAc (1.61 g, 26.8 mmol) and the mixture is stirred at 0° C. for 30 minutes. Sodium triacetoxyborohydride (10.3 g, 48.6 mmol) is added in portions. The resulting mixture is stirred at 25° C. for 16 hours. The reaction mixture is poured into a saturated aqueous sodium hydrogen carbonate solution (500 mL) and extracted with EtOAc (3×300 mL). The combined organic extracts are washed with brine (200 mL), dried over anhydrous sodium sulfate, filtered, and concentrated to dryness. The residue is purified by silica-gel column chromatography eluting with DCM:MeOH (20:1) to give the title compound (9.00 g, 67.5 mass %, 45% yield) as an off white solid. ES/MS (ESI) m/z 553.1 [M+H]$^+$.

Preparation 24 tert-Butyl 4-[5-[(3S)-3-[(3-chloro-5-fluoro-phenyl)methylcarbamoyl]-3-hydroxy-2-oxo-pyrrolidin-1-yl]-2-pyridyl]piperazine-1-carboxylate

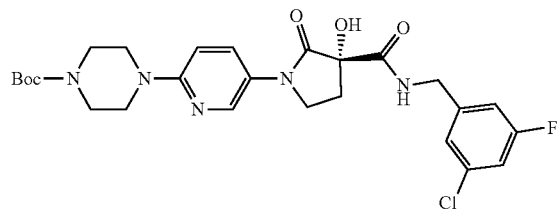 [SMILES: CC(C)(C)OC(=O)N1CCN(c2ccc(N3CC[C@](O)(C(=O)NCc4cc(F)cc(Cl)c4)C3=O)cn2)CC1]

A mixture of tert-butyl 4-(5-iodo-2-pyridyl)piperazine-1-carboxylate (300 mg, 0.771 mmol), (3R)—N-[(3-chloro-5-fluoro-phenyl)methyl]-3-hydroxy-2-oxo-pyrrolidine-3-carboxamide (242 mg, 0.848 mmol) and Cs$_2$CO$_3$ (739 mg, 2.31 mmol) in DMF (4.00 mL,) and ACN (2 mL) is stirred for 15 minutes under N$_2$. N,N'-Dimethylethylenediamine (20 mg, 0.231 mmol) and CuI (191 mg, 1.00 mmol) is added sequentially. The resulting mixture is stirred at 85° C. for 2 hours. The mixture is filtrated and the filtrate is poured into water (20 mL) and extracted with EtOAc (2×20 mL). The combined organic extracts are washed with saturated brine (10 mL) and dried over Na$_2$SO$_4$, filtered and the filtrate is evaporated to give the crude product. The crude product is purified by silica gel flash chromatography eluting with DCM:MeOH (100:0~20:1) to give the title compound (300 mg, 71.0%) as an off-white solid. ES/MS (m/z) 548.0 [M+H]$^-$.

Preparation 25

(3S)—N-[(3-Chloro-5-fluoro-phenyl)methyl]-3-hydroxy-2-oxo-1-(6-piperazin-1-yl-3-pyridyl)pyrrolidine-3-carboxamide

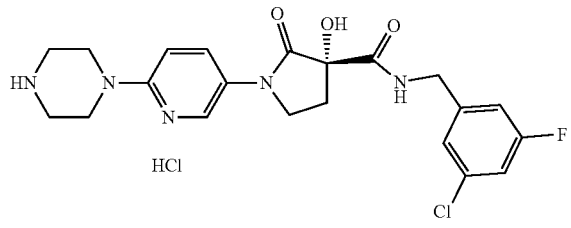 [SMILES: O=C(NCc1cc(F)cc(Cl)c1)[C@@]1(O)CCN(c2ccc(N3CCNCC3)nc2)C1=O ; Cl]

To a solution of tert-butyl 4-[5-[(3S)-3-[(3-chloro-5-fluoro-phenyl)methylcarbamoyl]-3-hydroxy-2-oxo-pyrrolidin-1-yl]-2-pyridyl]piperazine-1-carboxylate (300 mg, 0.5474 mmol) in MeOH (2.00 mL) is added dropwise HCl in MeOH (1.00 mL, 4.00 mmol, 4 mol/L). The reaction mixture is stirred at 15° C. for 3 hours and concentrated to give the title product (250 mg, 97.7%) as a light yellow solid. The product is used without further purification. ES/MS (m/z) 448.2 [M+H]$^+$.

Preparation 26 tert-Butyl N-[(2R,3S,5R)-2-(2,5-difluorophenyl)-5-[5-[3-hydroxy-2-oxo-3-[(2,3,5-trifluorophenyl)methylcarbamoyl]pyrrolidin-1-yl]isoindolin-2-yl]tetrahydropyran-3-yl]carbamate, isomer 1

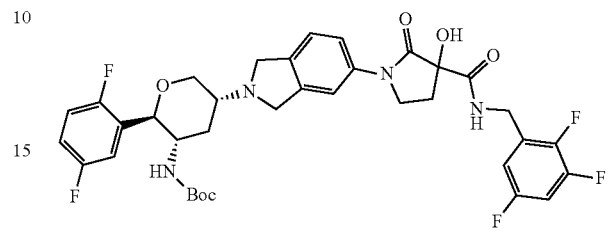

To a solution of tert-butyl N-[(2R,3S,5R)-5-(5-bromoisoindolin-2-yl)-2-(2,5-difluorophenyl)tetra hydropyran-3-yl]carbamate (4.00 g, 7.70 mmol) in ACN (40 mL) and DMF (40 mL) is added 3-hydroxy-2-oxo-N-[(2,3,5-trifluorophenyl)methyl]pyrrolidine-3-carboxamide, isomer 1 (2.22 g, 7.70 mmol), CuI (1.91 g, 10.0 mmol), Cs$_2$CO$_3$ (5.01 g, 15.4 mmol) and N,N'-dimethylethylenediamine (0.204 g, 2.31 mmol), then the reaction mixture is purged with N$_2$ and stirred at 90° C. for 8 hours under a N$_2$ atmosphere. The reaction mixture is cooled to room temperature, diluted with EtOAc (200 mL), and washed with NH$_3$·H$_2$O (2×500 mL). The aqueous layer is extracted with EtOAc (2×200 mL). The combined organic extracts are washed with brine (2×500 mL), dried over anhydrous Na$_2$SO$_4$, and concentrated under reduced pressure to give the crude product as a brown solid. The crude product is purified by silica gel flash chromatography eluting with DCM:MeOH (50:1) to give the title compound (3.62 g, 4.65 mmol, 92 mass %, 60.4% yield) as a brown solid. ES/MS (m/z) 717.3 [M+H].

Preparation 27 tert-Butyl N-[(2R,3S,5R)-5-[4-[3-[(3,5-dichloro-2-fluoro-phenyl)methyl carbamoyl]-3-hydroxy-2-oxo-pyrrolidin-1-yl]pyrazol-1-yl]-2-(2,5-difluorophenyl)tetrahydropyran-3-yl]carbamate, isomer 1

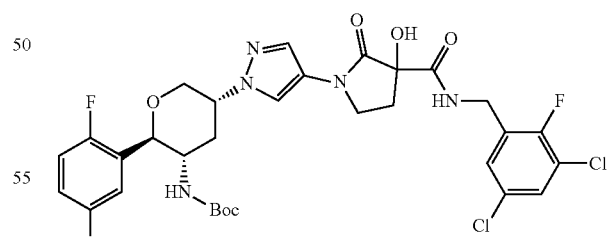

To a solution of N-[(3,5-dichloro-2-fluoro-phenyl)methyl]-3-hydroxy-2-oxo-pyrrolidine-3-carboxamide, isomer 1 (110 mg, 0.325 mmol) in ACN (3.00 mL) and DMF (3.00 mL) is added tert-butyl N-[(2R,3S,5R)-5-(5-bromoisoindol-2-yl)-2-(2,5-difluorophenyl)tetrahydropyran-3-yl]carbamate (200 mg, 0.240 mmol, 55 mass %), CuI (125 mg, 0.656 mmol), Cs$_2$CO$_3$ (325 mg, 0.997 mmol) and N,N'-dimethylethylenediamine (20.0 mg, 0.227 mmol). The reaction mixture is purged with nitrogen and stirred at 85° C. for 2 hours under a nitrogen atmosphere. The reaction mixture is cooled to room temperature, diluted with EtOAc (20 mL) and NH$_3$.H$_2$O (50 mL). The aqueous layer is extracted with EtOAc (2×20 mL). The combined organic extracts are washed with brine (3×50 mL), dried over anhydrous sodium sulfate, and concentrated under reduced pressure to give the crude product (300 mg) as a yellow solid. The crude product is purified by silica gel flash chromatography eluting with DCM:MeOH (20:1) to give the title product (65.0 mg, 90 mass %, 34.9% yield) as a pale yellow solid. ES/MS (ESI) m/z 598.1 [M−Boc]$^+$.

The following intermediates are prepared essentially by the method of tert-butyl N-[(2R,3S,5R)-2-(2,5-difluorophenyl)-5-[5-[3-hydroxy-2-oxo-3-[(2,3,5-trifluorophenyl)methylcarbamoyl]pyrrolidin-1-yl]isoindolin-2-yl]tetrahydropyran-3-yl]carbamate, isomer 1 using the appropriate reagents with the reaction temperature ranging from about 85° C. to 90° C. and reaction time varying from 2 to 16 hours.

TABLE 2

| Prep No. | Chemical Name | Structure | ES/MS (m/z) (M + H)$^+$ |
|---|---|---|---|
| 27 | tert-Butyl N-[(2R,3S,5R)-2-(2,5-difluorophenyl)-5-[4-[5-[3-[(2,3-difluorophenyl)methylcarbamoyl]-3-hydroxy-2-oxo-pyrrolidin-1-yl]pyrimidin-2-yl]piperazin-1-yl]tetrahydropyran-3-yl]carbamate, isomer 1 | 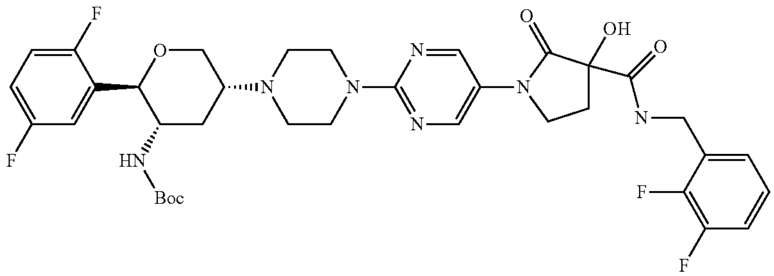 [SMILES: CC(C)(C)OC(=O)N[C@H]1C[C@@H](N2CCN(c3ncc(N4CCC(O)(C(=O)NCc5cccc(F)c5F)C4=O)cn3)CC2)CO[C@@H]1c1cc(F)ccc1F] | 744.2 |
| 28 | tert-Butyl N-[(2R,3S,5R)-5-[4-[3-[(3-chloro-5-fluorophenyl)methylcarbamoyl]-3-hydroxy-2-oxo-pyrrolidin-1-yl]pyrazol-1-yl]-2-(2,5-difluorophenyl)tetrahydropyran-3-yl]carbamate, isomer 1 | 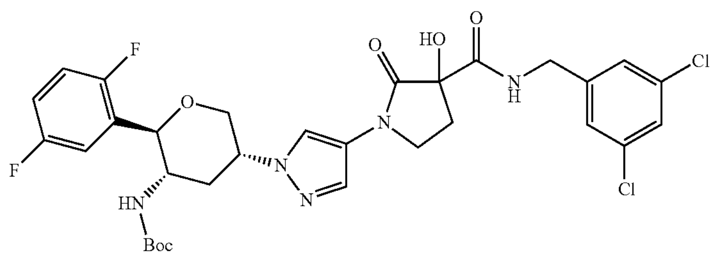 [SMILES: CC(C)(C)OC(=O)N[C@H]1C[C@@H](n2cc(N3CCC(O)(C(=O)NCc4cc(Cl)cc(Cl)c4)C3=O)cn2)CO[C@@H]1c1cc(F)ccc1F] | 580.0 [M + H − 100]$^+$ |
| 29 | tert-Butyl N-[(2R,3S,5R)-5-[4-[(3S)-3-[(3-chloro-5-fluorophenyl)methylcarbamoyl]-3-hydroxy-2-oxo-pyrrolidin-1-yl]triazol-2-yl]-2-(2,5-difluorophenyl)tetrahydropyran-3-yl]carbamate | 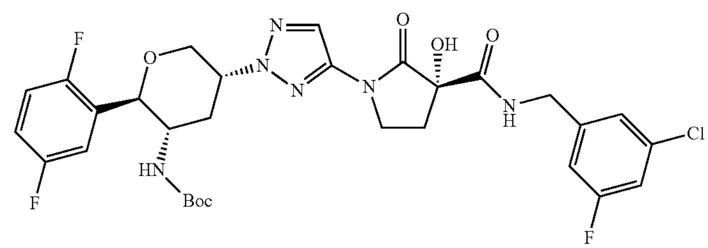 [SMILES: CC(C)(C)OC(=O)N[C@H]1C[C@@H](n2ncc(N3CC[C@](O)(C(=O)NCc4cc(F)cc(Cl)c4)C3=O)n2)CO[C@@H]1c1cc(F)ccc1F] | 687.2 [M + Na]$^+$ |
| 30 | tert-Butyl N-[(2R,3S,5R)-5-[3-[(3S)-3-[(3-chloro-5-fluorophenyl)methylcarbamoyl]-3-hydroxy-2-oxo-pyrrolidin-1-yl]pyrazol-1-yl]-2-(2,5-difluorophenyl)tetrahydropyran-3-yl]carbamate | 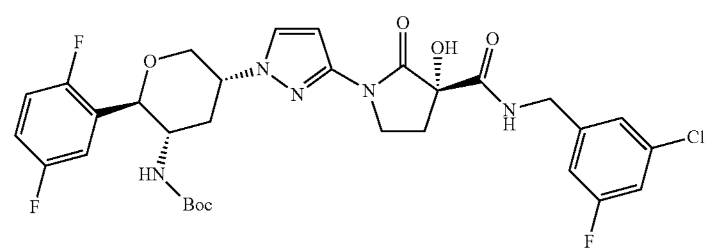 [SMILES: CC(C)(C)OC(=O)N[C@H]1C[C@@H](n2ccc(N3CC[C@](O)(C(=O)NCc4cc(F)cc(Cl)c4)C3=O)n2)CO[C@@H]1c1cc(F)ccc1F] | 686.1 [M + Na]$^+$ |
| | tert-Butyl N-[(2R,3S,5R)-2-(2,5-difluorophenyl)-5-[4-[5-[3-hydroxy-2-oxo-3-[(2,3,5-trifluorophenyl)methylcarbamoyl]pyrrolidin-1-yl]pyrimidin-2-yl]piperazin-1-yl]tetrahydropyran-3-yl]carbamate, isomer 1 | | 762.1 [M + H]$^+$ |

TABLE 2-continued

| Prep No. | Chemical Name | Structure | ES/MS (m/z) (M + H)+ |
|---|---|---|---|
| | tert-Butyl N-[(2R,3S,5R)-2-(2,5-difluorophenyl)-5-[4-[3-[(2,3-difluorophenyl)methylcarbamoyl]-3-hydroxy-2-oxo-pyrrolidin-1-yl]triazol-2-yl]tetrahydropyran-3-yl]carbamate, isomer 1 | | 671.2 [M + Na]+ |
| | tert-Butyl N-[(2R,3S,5R)-2-(2,5-difluorophenyl)-5-[4-[3-hydroxy-2-oxo-3-[(2,3,5-trifluorophenyl)methylcarbamoyl]pyrrolidin-1-yl]triazol-2-yl]tetrahydropyran-3-yl]carbamate, isomer 1 | | 689.1 [M + Na]+ |
| | tert-Butyl N-[(2R,3S,5R)-5-[4-[3-[(3,5-dichloro-2-fluorophenyl)methylcarbamoyl]-3-hydroxy-2-oxo-pyrrolidin-1-yl]triazol-2-yl]-2-(2,5 difluorophenyl)tetrahydropyran-3-yl]carbamate, isomer 1 | | 721.1 [M + Na]+ |
| | tert-Butyl N-[(2R,3S,5R)-5-[3-[3-[(3,5-dichloro-2-fluorophenyl)methylcarbamoyl]-3-hydroxy-2-oxo-pyrrolidin-1-yl]pyrazol-1-yl]-2-(2,5-difluorophenyl)tetrahydropyran-3-yl]carbamate, isomer 1 | | 720.1 [M + Na]+ |
| | tert-Butyl N-[(2R,3S,5R)-2-(2,5-difluorophenyl)-5-[3-[3-hydroxy-2-oxo-3-[(2,3,5-trifluorophenyl)methylcarbamoyl]pyrrolidin-1-yl]pyrazol-1-yl]tetrahydropyran-3-yl]carbamate, isomer 1 | | 688.2 [M + Na]+ |

Alternate Preparation 27 tert-Butyl N-[(2R,3S,5R)-5-(4-bromopyrazol-1-yl)-2-(2,5-difluorophenyl)tetrahydropyran-3-yl]carbamate (15.01 g) is dissolved in anhydrous 1,4-dioxane (226 mL) under a nitrogen atmosphere. N-[(3,5-Dichloro-2-fluoro-phenyl)methyl]-3-hydroxy-2-oxo-pyrrolidine-3-carboxamide, isomer 1 (11.71 g), cesium carbonate (19.21 g), sodium iodide (8.34 g), and cuprous iodide (1.247 g) are then added to the mixture under a nitrogen atmosphere. The mixture is degassed five times under nitrogen. Trans-N,N'-dimethylcyclohexane-1,2-diamine (1.60 mL) is added and the mixture is heated for 24 hours at 105° C. The mixture is diluted with EtOAc (226 mL), stirred for 5 minutes, and filtered through diatomaceous earth. Ammonium chloride saturated aqueous solution (226 mL, 226 mL) is added to the filtrate and the mixture is stirred at 22° C. for 30 minutes. The organic layer is isolated, washed with ammonium chloride saturated aqueous solution (4×226 mL) and evaporated to dryness. The residue is purified with silica gel filtration eluting with a gradient of 0% to 40% DCM in methyl-tert-butyl ether to give the title compound as an off white solid. MS (m/z): 598 [M+H]

Preparation 31 tert-Butyl N-[(2R,3S)-5-[4-[5-[(3S)-3-[(3-chloro-5-fluoro-phenyl)methylcarbamoyl]-3-hydroxy-2-oxo-pyrrolidin-1-yl]-2-pyridyl]piperazin-1-yl]-2-(2,5-difluorophenyl)tetrahydropyran-3-yl]carbamate

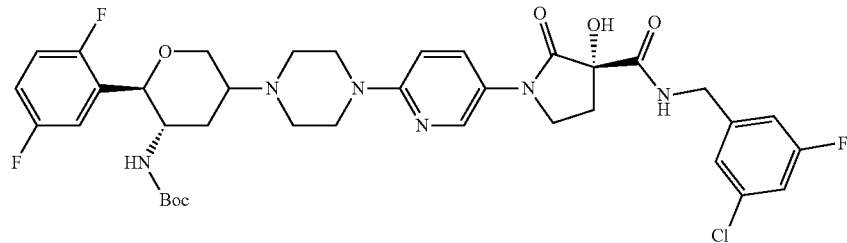 [SMILES: CC(C)(C)OC(=O)N[C@H]1CC(N2CCN(c3ccc(N4CC[C@](O)(C(=O)NCc5cc(F)cc(Cl)c5)C4=O)cn3)CC2)CO[C@@H]1c1cc(F)ccc1F]

To a solution of (3S)—N-[(3-chloro-5-fluoro-phenyl)methyl]-3-hydroxy-2-oxo-1-(6-piperazin-1-yl-3-pyridyl)pyrrolidine-3-carboxamide (200 mg, 0.4465 mmol) and tert-butyl N-[(2R,3S)-2-(2,5-difluorophenyl)-5-oxo-tetrahydropyran-3-yl]carbamate (175 mg, 0.536 mmol) in DMAc (4.00 mL) is added triethylamine (90.2 mg, 0.8931 mmol). The mixture is stirred at room temperature for 15 minutes to give a clear solution. HOAc (80.4 mg, 1.34 mmol) is added and the mixture is stirred for 60 minutes. Sodium triacetoxyborohydride (376.8 mg, 1.79 mmol) is added to the mixture at −10° C., the mixture is stirred at 16° C. for 16 hours. The mixture is diluted with EtOAc (2×100 mL) and washed with saturated brine (2×50 mL). The organic layer is dried over $Na_2SO_4$, filtered, and evaporated to give the crude product. The crude product is purified by silica gel flash chromatography eluting with DCM:MeOH (100:0~20:1~10:1) to give the title product (130 mg, 38.35%) as a light yellow solid. ES/MS (m/z) 759.1 [M+H]$^+$.

Preparation 32 tert-Butyl N-[(2R,3S,5R)-5-[4-[5-[(3S)-3-[(3-chloro-5-fluoro-phenyl)methylcarb amoyl]-3-hydroxy-2-oxo-pyrrolidin-1-yl]pyrimidin-2-yl]-3,6-dihydro-2H-pyridin-1-yl]-2-(2,5-difluorophenyl)tetrahydropyran-3-yl]carbamate A solution of tert-butyl N-[(2R,3S,5R)-5-[4-(5-bromopyrimidin-2-yl)-3,6-dihydro-2H-pyridin-1-yl]-2-(2,5-difluorophenyl)tetrahydropyran-3-yl]carbamate (8.00 g, 14.5 mmol), (3R)—N-[(3-chloro-5-fluoro-phenyl)methyl]-3-hydroxy-2-oxo-pyrrolidine-3-carboxamide (4.16 g, 14.5 mmol) and $Cs_2CO_3$ (14.2 g, 43.5 mmol) in DMF (160 mL) and ACN (80.0 mL) is degassed with a stream of $N_2$ for 15 minutes. N,N'-Dimethylmethanediamine (384 mg, 4.35 mmol) and CuI (3.59 g, 18.9 mmol) are added sequentially and the resulting mixture is stirred at 85° C. for 4 hours. Concentrated ammonium hydroxide (80 mL) and water (400 mL) are added. The mixture is extracted with EtOAc (3×300 mL) and the combined organic extracts are washed with saturated brine (200 ml), dried over anhydrous sodium sulfate, filtered, and concentrated to dryness. The residue is purified by silica gel flash chromatography eluting with DCM:MeOH (10:1) to give a mixture (7.0 g) as a yellow solid. The solid is purified by Prep-HPLC (column: Phenomenex Synergi Max-RP 250*50 mm*10 μm, mobile phase:15-56% B (A=0.1% TFA, B=ACN), flow rate: 25 mL/min, UV Detector 220 nm) to give the title product (3.5 g) as a yellow solid. Then the solid is further purified by Chiral SFC to give the title compound (2.40 g, 21%, $R_t$=1.893 min) as a yellow solid. ES/MS (ESI) m/z 757.3 [M+H]$^-$.

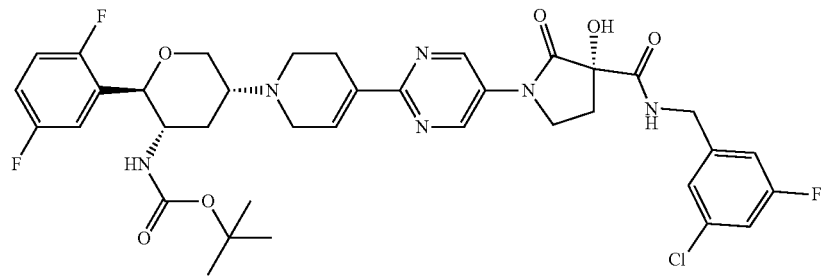 [SMILES: CC(C)(C)OC(=O)N[C@H]1C[C@@H](N2CC=C(c3ncc(N4CC[C@](O)(C(=O)NCc5cc(F)cc(Cl)c5)C4=O)cn3)CC2)CO[C@@H]1c1cc(F)ccc1F]

EXAMPLE 1

1-[2-[(3R,5S,6R)-5-Amino-6-(2,5-difluorophenyl)tetrahydropyran-3-yl]isoindolin-5-yl]-3-hydroxy-2-oxo-N-[(2,3,5-trifluorophenyl)methyl]pyrrolidine-3-carboxamie, isomer 1 hydrochloride

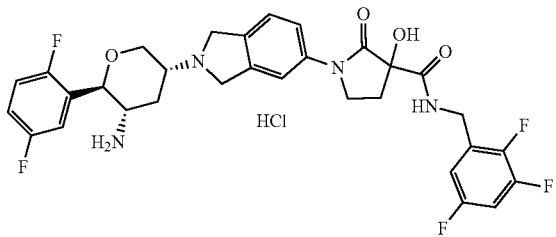 [SMILES: N[C@H]1C[C@@H](N2Cc3ccc(N4CCC(O)(C(=O)NCc5cc(F)cc(F)c5F)C4=O)cc3C2)CO[C@@H]1c1cc(F)ccc1F ; Cl]

To a solution of tert-butyl N-[(2R,3S,5S)-5-[6-[3-[(3-chloro-5-fluoro-phenyl)methylcarbamoyl]-3-hydroxy-2-oxo-pyrrolidin-1-yl]pyrazin-2-yl]-2-(2,5-difluorophenyl)tetrahydropyran-3-yl]carbamate, isomer 1 (3.62 g, 4.65 mmol, 92 mass %) in EtOAc (20 mL) is added HCl in EtOAc (40 mL, 4.0 mol/L) at 10° C., the reaction mixture is stirred at 10° C. for 1 hour and the mixture is concentrated to dryness. The crude material is purified by pre-HPLC using a gradient of solvent (column: Phenomenex Synergi C18 150*25*10 μm, condition: 20-50% B (A: water/0.05% HCl, B: ACN, flow rate: 100 mL/min) to give the title product. Fractions containing the desired product are concentrated to 50 mL of water. The solution is lyophilized to give the title compound (2.51 g, 3.84 mmol, 82.7% yield) as a white solid. ES/MS (m/z) 617.3 [M+H], $^1$H NMR (400 MHz, $d_4$-MeOH) δ 8.82 (t, J=6.0 Hz, 1H), 7.90 (br. s., 1H), 7.72 (d, J=8.3 Hz, 1H), 7.50 (d, J=8.3 Hz, 1H), 7.36 (d, J=3.3 Hz, 1H), 7.25 (d, J=4.5 Hz, 2H), 7.11-6.97 (m, 2H), 4.87-4.72 (m, 5H), 4.63-4.44 (m, 3H), 4.18-3.89 (m, 4H), 3.73 (t, J=10.8 Hz, 1H), 2.94 (d, J=5.3 Hz, 1H), 2.80-2.70 (m, 1H), 2.36-2.20 (m, 2H).

The following compounds are prepared essentially by the method of 1-[2-[(3R,5S,6R)-5-amino-6-(2,5-difluorophenyl)tetrahydropyran-3-yl]isoindolin-5-yl]-3-hydroxy-2-oxo-N-[(2,3,5-trifluorophenyl)methyl]pyrrolidine-3-carboxamide, isomer 1 hydrochloride

TABLE 3

| Ex No. | Chemical Name | Structure | ES/MS (m/z) (M + 1) |
|---|---|---|---|
| 2 | 1-[2-[(3R,5S,6R)-5-Amino-6-(2,5-difluorophenyl)tetrahydropyran-3-yl]isoindolin-5-yl]-N-[(2,3-difluorophenyl)methyl]-3-hydroxy-2-oxo-pyrrolidine-3-carboxamide, iosmer 1 hydrochloride | 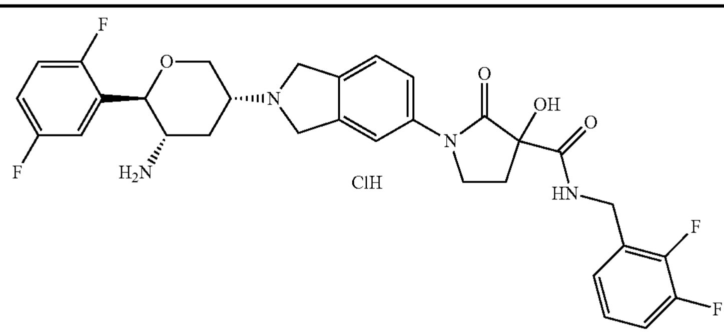 | 599.2 |

EXAMPLE 3

1-[2-[4-[(3R,5S,6R)-5-Amino-6-(2,5-difluorophenyl)tetrahydropyran-3-yl]piperazin-1-yl]pyrimidin-5-yl]-N-[(2,3-difluorophenyl)methyl]-3-hydroxy-2-oxo-pyrrolidine-3-carboxamide, isomer 1 hydrochloride

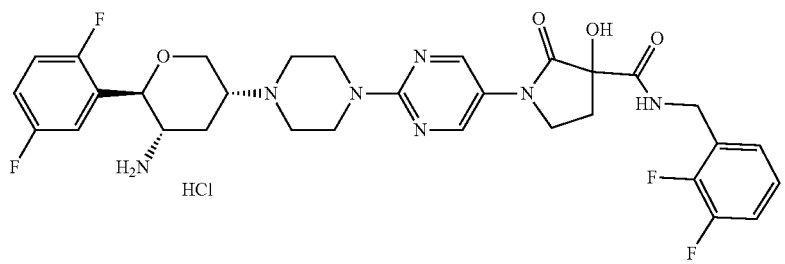 [SMILES: N[C@H]1C[C@@H](N2CCN(c3ncc(N4CCC(O)(C(=O)NCc5cccc(F)c5F)C4=O)cn3)CC2)CO[C@@H]1c1cc(F)ccc1F ; Cl]

To a solution of tert-butyl N-[(2R,3S,5R)-2-(2,5-difluorophenyl)-5-[4-[5-[3-[(2,3-difluorophenyl)methylcarbamoyl]-3-hydroxy-2-oxo-pyrrolidin-1-yl]pyrimidin-2-yl]piperazin-1-yl]tetrahydropyran-3-yl]carbamate (3.00 g, 3.95 mmol) in EtOAc (10 mL) is added HCl (20 mL, 4.0 mol/L in EtOAc) at 8° C., the reaction mixture is stirred at 8° C. for 1.5 hours. The precipitate is collected by filtration. The solid is dissolved in water (100 mL) and lyophilized to give the title compound (2.60 g, 96.2%) as a white solid. ES/MS (m/z) 644.1 [M+H]. $^1$H NMR (400 MHz, d$_4$-MeOH) δ 8.79 (s, 2H), 7.36-7.29 (m, 1H), 7.28-7.21 (m, 2H), 7.19-7.07 (m, 3H), 4.75 (d, J=12.0 Hz, 1H), 4.69-4.44 (m, 4H), 4.05-3.34 (m, 12H), 2.91 (d, J=8.0 Hz, 1H), 2.80-2.70 (m, 1H), 2.35-2.19 (m, 2H).

The following compound is prepared essentially by the method of 1-[2-[4-[(3R,5S,6R)-5-amino-6-(2,5-difluorophenyl)tetrahydropyran-3-yl]piperazin-1-yl]pyrimidin-5-yl]-N-[(2,3-difluorophenyl)methyl]-3-hydroxy-2-oxo-pyrrolidine-3-carboxamide, isomer 1 hydrochloride

TABLE 4

| Ex No. | Chemical Name | Structure | ES/MS (m/z) (M + 1) |
|---|---|---|---|
| 4 | 1-[2-[4-[(3R,5S,6R)-5-Amino-6-(2,5-difluorophenyl)tetrahydropyran-3-yl]piperazin-1-yl]pyrimidin-5-yl]-3-hydroxy-2-oxo-N-[(2,3,5-trifluorophenyl)methyl]pyrrolidine-3-carboxamide, isomer 1 hydrochloride | 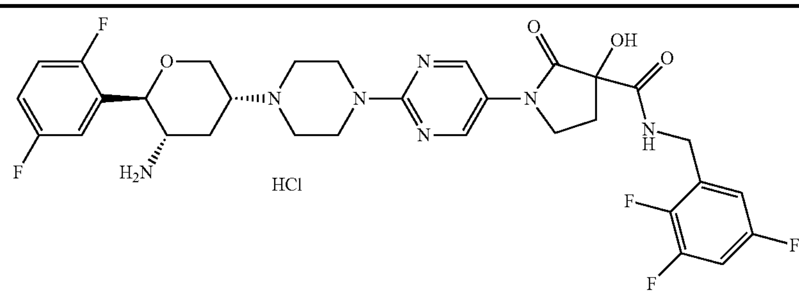 | 662.1 |

EXAMPLE 5

(3S)-1-[6-[4-[(3S,5S,6R)-5-Amino-6-(2,5-difluorophenyl)tetrahydropyran-3-yl]piperazin-1-yl]-3-pyridyl]-N-[(3-chloro-5-fluoro-phenyl)methyl]-3-hydroxy-2-oxo-pyrrolidine-3-carboxamide, hydrochloride

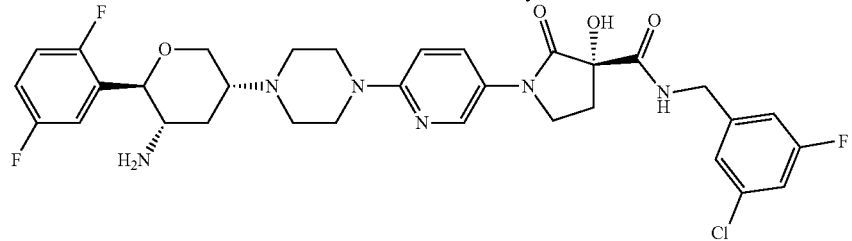

To a solution of tert-butyl N-[(2R,3S)-5-[4-[5-[(3S)-3-[(3-chloro-5-fluoro-phenyl)methylcarbamoyl]-3-hydroxy-2-oxo-pyrrolidin-1-yl]-2-pyridyl]piperazin-1-yl]-2-(2,5-difluorophenyl)tetrahydropyran-3-yl]carbamate (130 mg, 0.159 mmol, 93.0 mass %) in EtOAc (2.00 mL) is added HCl in EtOAc (2.00 mL, 8.00 mmol, 4.00 mol/L). The reaction mixture is stirred at 26° C. for 3 hours. The reaction mixture is filtered and evaporated to give the product as a mixture. The mixture is separated by SFC (Phenomenex AS 250*30 mm*5 μm: 40% B (B=0.05% diethylamine in MeOH), flow rate: 50 mL/min). The product is purified by preparative HPLC (Boston Green ODS 150*30 mm*5 μm: 10-40% B (A=0.05% HCl water, B=ACN), flow rate: 25 mL/min). Fractions containing the desired compound are evaporated to dryness to give the title product (30.1 mg, 28.4%). ES/MS (ESI) m/z 659.2 [M+H]$^+$, $^1$H NMR (400 MHz, d$_4$-MeOH) δ 8.63 (s, 1H), 8.40 (d, J=9.2 Hz, 1H), 7.49 (d, J=9.2 Hz, 1H), 7.38-7.18 (m, 4H), 7.08 (t, J=9.2 Hz, 2H), 4.77 (d, J=10.0 Hz, 1H), 4.66-4.48 (m, 2H), 4.42-4.34 (m, 1H), 4.24-3.86 (m, 8H), 3.70 (d, J=5.6 Hz, 5H), 3.02-2.87 (m, 1H), 2.83-2.62 (m, 1H), 2.40-2.17 (m, 2H)

EXAMPLE 6

1-[1-[(3R,5S,6R)-5-Amino-6-(2,5-difluorophenyl)tetrahydropyran-3-yl]pyrazol-4-yl]-N-[(3,5-dichlorophenyl)methyl]-3-hydroxy-2-oxo-pyrrolidine-3-carboxamide, isomer 1 hydrochloride

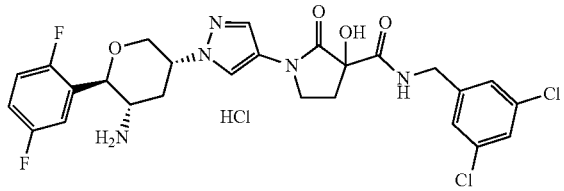 [SMILES: N[C@H]1C[C@@H](n2cc(N3CCC(O)(C(=O)NCc4cc(Cl)cc(Cl)c4)C3=O)cn2)CO[C@@H]1c1cc(F)ccc1F ; Cl]

To a solution of tert-butyl N-[(2R,3S,5R)-5-[4-[3-[(3-chloro-5-fluoro-phenyl)methylcarbamoyl]-3-hydroxy-2-oxo-pyrrolidin-1-yl]pyrazol-1-yl]-2-(2,5-difluorophenyl)tetrahydropyran-3-yl]carbamate, isomer 1 (2.90 g, 4.13 mmol) in EtOAc (60.0 mL) is added HCl (4 mol/L) in EtOAc (30.0 mL) slowly. The resulting mixture is stirred at 18° C. for 2 hours. The solvent is evaporated under reduced pressure. The crude product is washed with EtOAc (10 mL) to give the title compound (2.04 g, 78.5%) as a white solid. ES/MS (m/z) 580.0 [M+H]$^+$, $^1$H NMR (400 MHz, d$_4$-MeOH) δ 8.20 (s, 1H), 7.83 (s, 1H), 7.40-7.34 (m, 1H), 7.34-7.29 (m, 3H), 7.28-7.21 (m, 2H), 4.80-4.67 (m, 2H), 4.51-4.42 (m, 1H), 4.41-4.24 (m, 2H), 3.94-3.81 (m, 3H), 3.73-3.61 (m, 1H), 2.80-2.64 (m, 2H), 2.44 (q, J=12.1 Hz, 1H), 2.29 (td, J=8.0, 13.4 Hz, 1H).

EXAMPLE 7

1-[1-[(3R,5S,6R)-5-Amino-6-(2,5-difluorophenyl)tetrahydropyran-3-yl]pyrazol-4-yl]-N-[(3,5-dichloro-2-fluoro-phenyl)methyl]-3-hydroxy-2-oxo-pyrrolidine-3-carboxamide, isomer 1 hydrochloride

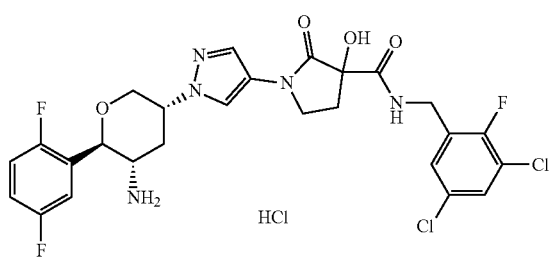 [SMILES: N[C@H]1C[C@@H](n2cc(N3CCC(O)(C(=O)NCc4cc(Cl)cc(Cl)c4F)C3=O)cn2)CO[C@@H]1c1cc(F)ccc1F ; Cl]

To a solution of tert-butyl N-[(2R,3S,5R)-5-[4-[3-[(3,5-dichloro-2-fluoro-phenyl)methylcarbamoyl]-3-hydroxy-2-oxo-pyrrolidin-1-yl]pyrazol-1-yl]-2-(2,5-difluorophenyl)tetrahydropyran-3-yl]carbamate, isomer 1 (65.0 mg, 0.0838 mmol, 90 mass %) in EtOAc (5.00 mL) is added HCl (10.0 mL, 40.0 mmol, 4 mol/L) at 0° C. The reaction mixture is stirred at 10° C. for 30 minutes. The solvent is removed under reduced and the crude product is purified by pre-HPLC (Column: Boston Green ODS 150*30 mm*5 μm with the following conditions: 25~55% B (A: water (0.05% HCl), B: ACN, R$_t$=0.578 min); flow rate:25 mL/min) to give the title product, which is dissolved in water/CH$_3$CN (v/v, 2:1, 15 mL) and lyophilized to give the title product (41.9 mg, 77.2%) as a white solid. $^1$H NMR (400 MHz, d$_4$-MeOH) δ 8.19 (s, 1H), 7.81 (s, 1H), 7.45 (dd, J=2.6, 6.1 Hz, 1H), 7.41-7.32 (m, 2H), 7.30-7.18 (m, 2H), 4.79-4.69 (m, 2H), 4.58-4.40 (m, 2H), 4.29 (dd, J=3.3, 11.0 Hz, 1H), 3.93-3.81 (m, 3H), 3.72-3.62 (m, 1H), 2.81-2.64 (m, 2H), 2.44 (q, J=12.0 Hz, 1H), 2.29 (td, J=7.9, 13.5 Hz, 1H) ES/MS (ESI) m/z 597.9 [M+H]$^+$.

EXAMPLE 8

(3S)-1-[2-[(3R,5S,6R)-5-Amino-6-(2,5-difluorophenyl)tetrahydropyran-3-yl]triazol-4-yl]-N-[(3-chloro-5-fluoro-phenyl)methyl]-3-hydroxy-2-oxo-pyrrolidine-3-carboxamide, hydrochloride

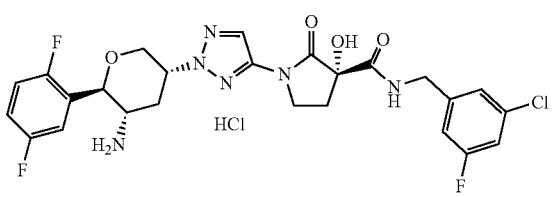 [SMILES: N[C@H]1C[C@@H](n2ncc(N3CC[C@](O)(C(=O)NCc4cc(F)cc(Cl)c4)C3=O)n2)CO[C@@H]1c1cc(F)ccc1F ; Cl]

To a solution of tert-butyl N-[(2R,3S,5R)-5-[4-[(3S)-3-[(3-chloro-5-fluoro-phenyl)methylcarbamoyl]-3-hydroxy-2-oxo-pyrrolidin-1-yl]triazol-2-yl]-2-(2,5-difluorophenyl)tetrahydropyran-3-yl]carbamate (1.50 g, 2.26 mmol) in EtOAc (20.0 mL) is slowly added HCl (4 mol/L) in EtOAc (20.0 mL). The resulting mixture is stirred at 25° C. for 1.5 hours. The mixture is concentrated to remove part of the solvent and the resulting precipitate is filtered to give the title compound (1.20 g, 86.5%) as an off white solid. ES/MS (m/z) 565.1 [M+H]$^+$. The title compound, combined with material prepared essentially the same (2.20 g, 3.66 mmol), is dissolved in a solution of water (32 mL) and ACN (8.0 mL). The solution is lyophilized to give the title compound (1.97 g, 87.9%) as an off white solid. ES/MS (m/z) 565.1 [M+H]$^+$, $^1$H NMR (400 MHz, d$_4$-MeOH) δ 8.17 (s, 1H), 7.44-7.37 (m, 1H), 7.32-7.23 (m, 2H), 7.21 (s, 1H), 7.12-7.03 (m, 2H), 5.04 (s, 1H), 4.79 (d, J=10.0 Hz, 1H), 4.55-4.35 (m, 3H), 4.07-3.88 (m, 3H), 3.79-3.69 (m, 1H), 2.91-2.74 (m, 2H), 2.49 (q, J=12.0 Hz, 1H), 2.39-2.27 (m, 1H).

The following compounds are prepared essentially by the method of (3S)-1-[2-[(3R,5S,6R)-5-amino-6-(2,5-difluorophenyl)tetrahydropyran-3-yl]triazol-4-yl]-N-[(3-chloro-5-fluoro-phenyl)methyl]-3-hydroxy-2-oxo-pyrrolidine-3-carboxamide, hydrochloride

TABLE 6

| Ex No. | Chemical Name | Structure | ES/MS (m/z) (M + 1) |
|---|---|---|---|
| 9 | 1-[2-[(3R,5S,6R)-5-Amino-6-(2,5-difluorophenyl)tetrahydropyran-3-yl]triazol-4-yl]-N-[(2,3-difluorophenyl)methyl]-3-hydroxy-2-oxo-pyrrolidine-3-carboxamide, isomer 1 hydrochloride | 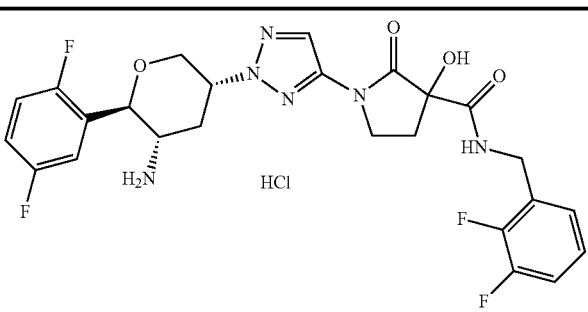 | 549.0 |
| 10 | 1-[2-[(3R,5S,6R)-5-Amino-6-(2,5-difluorophenyl)tetrahydropyran-3-yl]triazol-4-yl]-N-[(2,3-difluorophenyl)methyl]-3-hydroxy-2-oxo-pyrrolidine-3-carboxamide, isomer 1 hydrochloride | 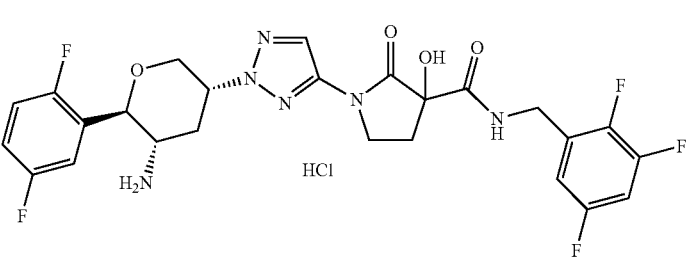 [SMILES: N[C@H]1C[C@@H](n2ncc(N3CCC(O)(C(=O)NCc4cc(F)cc(F)c4F)C3=O)n2)CO[C@@H]1c1cc(F)ccc1F ; Cl] | 567.1 |
| 11 | 1-[2-[(3R,5S,6R)-5-Amino-6-(2,5-difluorophenyl)tetrahydropyran-3-yl]triazol-4-yl]-N-[(3,5-dichloro-2-fluoro-phenyl)methyl]-3-hydroxy-2-oxo-pyrrolidine-3-carboxamide, isomer 1 hydrochloride | 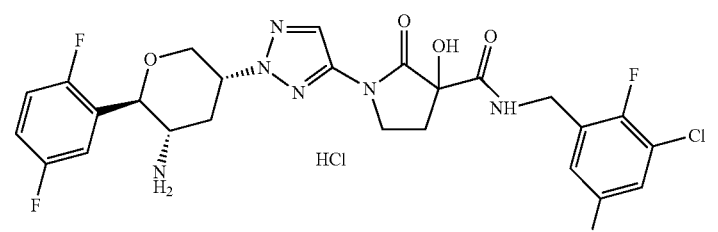 | 599.0 |

EXAMPLE 12

(3S)-1-[1-[(3R,5S,6R)-5-Amino-6-(2,5-difluorophenyl)tetrahydropyran-3-yl]pyrazol-3-yl]-N-[(3-chloro-5-fluoro-phenyl)methyl]-3-hydroxy-2-oxo-pyrrolidine-3-carboxamide, hydrochloride

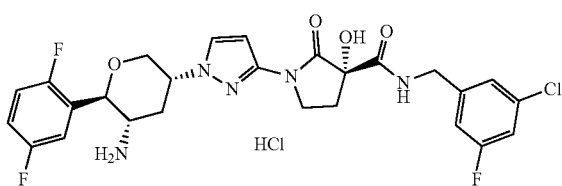 [SMILES: N[C@H]1C[C@@H](n2ccc(N3CC[C@](O)(C(=O)NCc4cc(F)cc(Cl)c4)C3=O)n2)CO[C@@H]1c1cc(F)ccc1F ; Cl]

To a solution of tert-butyl N-[(2R,3S,5R)-5-[3-[(3S)-3-[(3-chloro-5-fluoro-phenyl)methylcarbamoyl]-3-hydroxy-2-oxo-pyrrolidin-1-yl]pyrazol-1-yl]-2-(2,5-difluorophenyl)tetrahydropyran-3-yl]carbamate as a mixture (0.0800 g, 0.117 mmol) in EtOAc (10.0 mL) is slowly added HCl (4 mol/L) in EtOAc (10.0 mL). The mixture is stirred at 25° C. for 1.5 hours and concentrated. The crude material is purified by Prep-HPLC (column: Phenomenex Synergi C18 150*30 mm*4 μm, mobile phase: 20-40% B (A=0.05% HCl, B=ACN), flow rate: 25 mL/min, UV Detector 220 nm) to give the title compound (25.9 mg, 35.0%) as a white solid.
$^1$H NMR (400 MHz, d$_4$-MeOH) δ 7.71 (d, J=2.2 Hz, 1H), 7.39 (br. s., 1H), 7.30-7.19 (m, 3H), 7.08 (t, J=9.5 Hz, 2H), 6.82 (d, J=2.2 Hz, 1H), 4.80-4.64 (m, 2H), 4.55-4.35 (m, 2H), 4.29 (dd, J=4.4, 11.2 Hz, 1H), 4.09-3.89 (m, 3H), 3.74-3.62 (m, 1H), 2.78-2.62 (m, 2H), 2.50 (m, 1H), 2.32-2.20 (m, 1H).

The following compounds are prepared essentially by the method of (3S)-1-[1-[(3R,5S,6R)-5-amino-6-(2,5-difluorophenyl)tetrahydropyran-3-yl]pyrazol-3-yl]-N-[(3-chloro-5-fluoro-phenyl)methyl]-3-hydroxy-2-oxo-pyrrolidine-3-carboxamide, hydrochloride

TABLE 7

| Ex No. | Chemical Name | Structure | ES/MS (m/z) (M + 1) |
|---|---|---|---|
| 13 | 1-[2-[(3R,5S,6R)-5-Aamino-6-(2,5-difluorophenyl)tetrahydropyran-3-yl]-3,4-dihydropyrazol-3-yl]-N-[(3,5-dichloro-2-fluorophenyl)methyl]-3-hydroxy-2-oxo-pyrrolidine-3 carboxamide, isomer 1 hydrochloride | 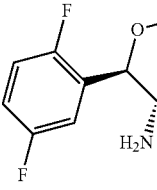 | 598.1 |
| 14 | 1-[1-[(3R,5S,6R)-5-Amino-6-(2,5-difluorophenyl)tetrahydropyran-3-yl]pyrazol-3-yl]-3-hydroxy-2-oxo-N-[(2,3,5-trifluorophenyl)methyl]pyrrolidine-3-carboxamide, isomer 1 hydrochloride | 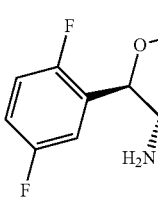 | 566.1 |
| 15 | 1-[1-[(3R,5S,6R)-5-Amino-6-(2,5-difluorophenyl)tetrahydropyran-3-yl]pyrazol-3-yl]-N-[(3,5-difluorophenyl)methyl]-3-hydroxy-2-oxo-pyrrolidine-3-carboxamide, isomer 1 hydrochloride | 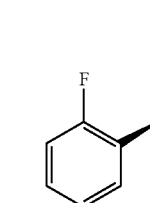 | 548.3 |
| 16 | 1-[1-[(3R,5S,6R)-5-Amino-6-(2,5-difluorophenyl)tetrahydropyran-3-yl]pyrazol-3-yl]-N-[(3-fluorophenyl)methyl]-3-hydroxy-2-oxo-pyrrolidine-3-carboxamide, isomer 1 hydrochloride | 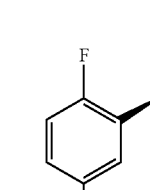 | 530.4 |

EXAMPLE 17

(3S)-1-[2-[1-[(3R,5S,6R)-5-Amino-6-(2,5-difluoro-phenyl)tetrahydropyran-3-yl]-3,6-dihydro-2H-pyridin-4-yl]pyrimidin-5-yl]-N-[(3-chloro-5-fluoro-phenyl)methyl]-3-hydroxy-2-oxo-pyrrolidine-3-carboxamide, hydrochloride

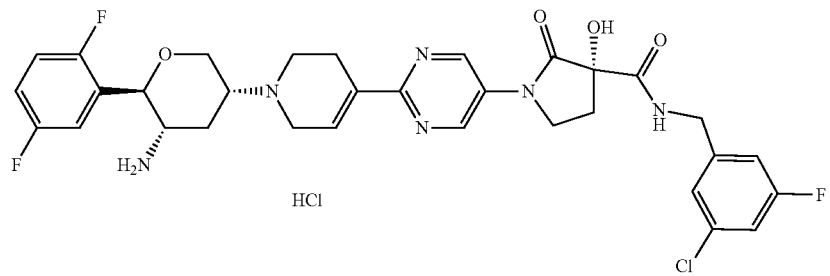 [SMILES: N[C@H]1C[C@@H](N2CC=C(c3ncc(N4CC[C@](O)(C(=O)NCc5cc(F)cc(Cl)c5)C4=O)cn3)CC2)CO[C@@H]1c1cc(F)ccc1F ; Cl]

To a solution of tert-butyl N-[(2R,3S,5R)-5-[4-[5-[(3S)-3-[(3-chloro-5-fluoro-phenyl)methylcarbamoyl]-3-hydroxy-2-oxo-pyrrolidin-1-yl]pyrimidin-2-yl]-3,6-dihydro-2H-pyridin-1-yl]-2-(2,5-difluorophenyl) tetrahydropyran-3-yl]carbamate (2.40 g, 3.17 mmol) in EtOAc (40.0 mL) is slowly added HCl (4 mol/L) in EtOAc (40.0 mL). The resulting mixture is stirred at 25° C. for 1.5 hours. The mixture is filtered and the solid is dissolved in 20% ACN/water (150 ml) and lyophilized to give the title compound (2.026 g, 91%) as a yellow solid. ES/MS (ESI) m/z 657.1 [M+H]$^+$, $^1$H NMR (400 MHz, d$_4$-MeOH) δ 9.22 (s, 2H), 7.40-7.33 (m, 1H), 7.32-7.19 (m, 4H), 7.12-7.04 (m, 2H), 4.79 (d, J=10.0 Hz, 1H), 4.67-4.58 (m, 1H), 4.55-4.35 (m, 2H), 4.24 (br. s., 2H), 4.15-3.83 (m, 5H), 3.72 (dt, J=3.8, 10.7 Hz, 1H), 3.62-3.39 (m, 1H), 3.27-3.03 (m, 2H), 2.98-2.87 (m, 1H), 2.84-2.77 (m, 1H), 2.42-2.19 (m, 2H)

Biological Assays

Enzymatic Activity Assay of MetAP2

The compounds exemplified herein are tested essentially as described below and exhibit an IC$_{50}$ for the human and mouse MetAP2 assay as shown in Table 1.

Full length MetAP2 (human and mouse) proteins are generated from Sf9 cells using procedure similar to that described in Biochemistry 2003, 42, 5035-5042. MetAP2 is purified in the presence of 5 mM MnCl$_2$ and 2 mM CoCl$_2$ respectively, and stored at −78° C. before use.

Inhibition of the catalytic activity of human and mouse MetAP2 by compounds in the present invention is measured by monitoring the formation of the product peptide (Gly-Lys-Val-Lys-Val-Gly-Val-Asn-Gly) from the substrate peptide (Met-Gly-Lys-Val-Lys-Val-Gly-Val-Asn-Gly) via LC/MS. The reaction is typically conducted by incubating the enzyme, test compound and substrate (150 μM) in an assay buffer (100 μl) (50 mM HEPES, 100 mM NaCl, 50 mg/mL BSA, 0.17 mM Triton™ X-100 at pH 7.5) for 40 minutes. After the reaction is stopped by the addition of ACN (200 μl), the levels of product and remaining substrate are quantified with a mass spectrometer. The IC$_{50}$ value is calculated typically from a 10-point dose titration curve using a 4-parameter equation.

The IC$_{50}$'s for the human and mouse MetAP2 assay for the exemplified Example compounds are lower than 1000 nM (See Table 8). An IC$_{50}$ for the human and mouse MetAP2 assay lower than 1000 nM supports that the exemplified compound inhibits MetAP2.

Enzymatic Activity Assay of DPP-4

Human DPP-4 ((39-766)-His) and mouse DPP-4 ((29-760)-His) are purified by gel chromatography for use in the assay. The final concentration of hDPP-4 and mDPP-4 in the assay is 0.04 nM and 0.22 nM respectively.

Inhibition of the catalytic activity of human and mouse DPP-4 by the compound in the present invention is monitored by the formation of product fluorescence AMC from substrate Gly-Pro-AMC (Sigma, G2761) on an Envision plate reader. The reaction is typically conducted by incubating the enzyme, test compound, and substrate (10 μM) in an assay buffer (75 μl) (0.01% BSA, 0.1 mM EDTA, 50 μM Tris-HCl, 0.01% Triton™-X100, 0.1 M NaCl at pH 7.5) for 30 minutes. After the reaction is stopped by the addition of ZnSO$_4$ (25 μl, 10 mM), the formation of fluorescent product AMC is measured on an Envision plate reader with the excitation wavelength at 355 nm and emission wavelength at 460 nm. The IC$_{50}$ value is calculated typically from a 10-point dose titration curve using the 4-parameter logistic equation. The IC$_{50}$ for the indazole compounds is shown in Table 5.

The IC$_{50}$'s for the exemplified Example compounds are lower than 1000 nM in the human and mouse DPP-4 assay and the results are shown in Table 2. The data support that the compounds inhibit DPP-4.

TABLE 8

$IC_{50}$ for MetAp2 and DPP-4.

| Example # | hDPP-4 $IC_{50}$ μM (SD, n)[a] | mDPP-4 $IC_{50}$ μM (SD, n)[a] | hMetAP2 $IC_{50}$ μM (SD, n)[a] | mMetAP2 $IC_{50}$ μM (SD, n)[a] |
|---|---|---|---|---|
| 1 | 0.00298 ± 0.00049, n = 4 | 0.00653 ± 0.00046, n = 4 | 0.0483 ± 0.0030, n = 2 | 0.0219 ± 0.0136, n = 2 |
| 2 | 0.00367 ± 0.00051, n = 2 | 0.00646 ± 0.00090, n = 2 | 0.0680 ± 0.0175, n = 2 | 0.0336 ± 0.0096, n = 2 |
| 3 | 0.0164 ± 0.0063, n = 2 | 0.0325 ± 0.0106, n = 2 | 0.155 ± 0.027, n = 2 | 0.103 ± 0.002, n = 2 |
| 4 | 0.0165 ± 0.0025, n = 2 | 0.0307 ± 0.0008, n = 2 | 0.125 ± 0.004, n = 2 | 0.111 ± 0.016, n = 2 |
| 5 | 0.0175 ± 0.0015, n = 2 | 0.0283 ± 0.0137, n = 3 | 0.125 ± 0.010, n = 2 | 0.0802 ± 0.0059, n = 2 |
| 6 | 0.00191 ± 0.00004, n = 2 | 0.000474 | 0.261 ± 0.024, n = 2 | 0.123 ± 0.019, n = 3 |
| 7 | 0.00188 ± 0.00053, n = 4 | 0.000498 | 0.0814 ± (0.0338, n = 4 | 0.0368 ± 0.0158, n = 4 |
| 8 | 0.00167 ± 0.00015, n = 3 | 0.000564 | 0.0952 ± 0.0350, n = 2 | 0.0480 ± 0.0016, n = 2 |
| 9 | 0.00271 | 0.00357 | 0.293 | 0.154 |
| 10 | 0.00296 | <0.00152 | 0.204 ± 0.012, n = 2 | 0.0947 ± 0.0110, n = 2 |
| 11 | <0.00152 | <0.00152 | 0.0208 ± 0.0037, n = 2 | 0.0128 ± 0.0060, n = 2 |
| 12 | 0.00343 ± 0.00171, n = 3 | 0.00264 ± 0.00152, n = 2 | 0.0562 ± 0.0224, n = 4 | 0.0321 ± 0.0062, n = 4 |
| 13 | 0.00327 | 0.00203 | 0.015 | 0.0106 |
| 14 | 0.00756 ± 0.00005, n = 2 | 0.0131 ± 0.0005, n = 3 | 0.0334 ± 0.0101, n = 3 | 0.0292 ± 0.0022, n = 3 |
| 15 | 0.00623 ± 0.00017, n = 2 | 0.00773 ± 0.00041, n = 2 | 0.0537 ± 0.0133, n = 2 | 0.0305 ± 0.0027, n = 2 |
| 16 | 0.00676 | 0.0186 | 0.106 | 0.0603 |
| 17 | 0.0147 ± 0.0033, n = 3 | 0.0255 ± 0.0053, n = 4 | 0.430 ± 0.108, n = 3 | 0.283 ± 0.058, n = 3 |

Therapeutic Weight Loss Effect Measurement of Compounds

To determine the therapeutic weight loss effects and improvement of metabolic parameters, the compound from the invention is tested in a HFD feeding induced obese mouse model (DIO mice). In this model, C57/B16J male mouse is fed with the 60% HFD (D12492i, Research Diets) for 16~28 weeks to establish obesity with body weight reaching around 50 g. The mice will gradually increase their body weight to about 50 g and maintain that weight in this obese state. The test compound (via the vehicle of 0.5% HEC plus 0.25% Tween®-80 at 5 mL/kg) is administered orally to the obese DIO mice once or twice daily throughout the study duration. The dose-dependent weight loss of obese DIO mice for Example 1 of the oral treatment at 20 mg/kg once daily is about 8.9% weight loss compared to the vehicle group at day 14. The dose-dependent weight loss of obese DIO mice for Example 7 of the oral treatment at 40 mg/kg once daily is about 4.8% weight loss compared to the vehicle group at day 14. The data support that the compound of Example 1 and Example 7 is associated with desired weight loss and could offer a therapeutic weight loss effect.

DPP-4 Pharmacodynamics Assay in Mouse

To determine the in vivo DPP-4 inhibition by MetAP2 plus DPP-4 dual inhibitor compounds, C57B/L6 lean mice are administrated with the compound in fed states and then DPP-4 target engagement in plasma is measured.

Animals are weighed and randomized by body weight. Each mouse is dosed once via oral gavage with vehicle or testing compound formulated with vehicle at 3 pm. The mice are fasted for 18 hours after dosing before termination at 9 am the next day. Blood samples are collected at 2 hours after dosing and upon termination. EDTA-$K_2$ at final concentration of 5 mM is used as an anticoagulant. Plasma, isolated from the blood samples, is used to determine the plasma DPP-4 enzyme activity.

Plasma DPP-4 enzyme activity in the present invention is monitored by the formation rate of paranitroaniline from substrate glycyl-prolyl-paranitroaniline (Nanjing Norris, 103213-34-9) via Spectramax M5 microplate reader. The reaction is typically conducted by incubating the plasma (40 μl) and substrate (400 μM) in assay buffer (100 μL) (100 mM HEPES, 0.1 mg/ml BSA at pH 7.5) at 37° C. and measuring the release of paranitroaniline by an increase in absorbance at 390 nm over time. The plasma DPP-4 activity is calculated from the reaction velocity. The percentage plasma DPP-4 inhibition is normalized against plasma DPP-4 activity in the vehicle group, which is set as 0% inhibition.

The plasma DPP-4 inhibition for Example 1 under the assay conditions is 85% at 2 hours after an oral dose of 20 mg/kg. The plasma DPP-4 inhibition for Example 7 under the assay conditions is 75% at 2 hours after an oral dose of 20 mg/kg. The data support that the compounds of Example 1 and Example 7 are associated with desired DPP-4 inhibition that could yield therapeutic glycemic control.

What is claimed is:

1. A compound of the Formula

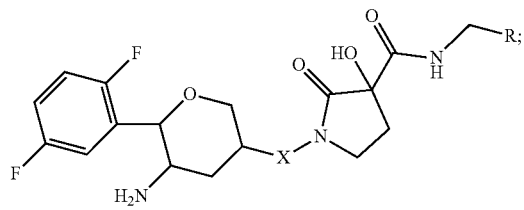

wherein X is selected from the group consisting of

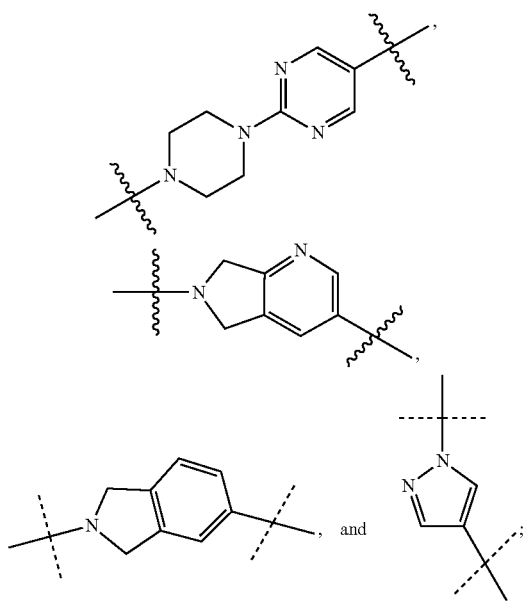

and
R is selected from the group consisting of

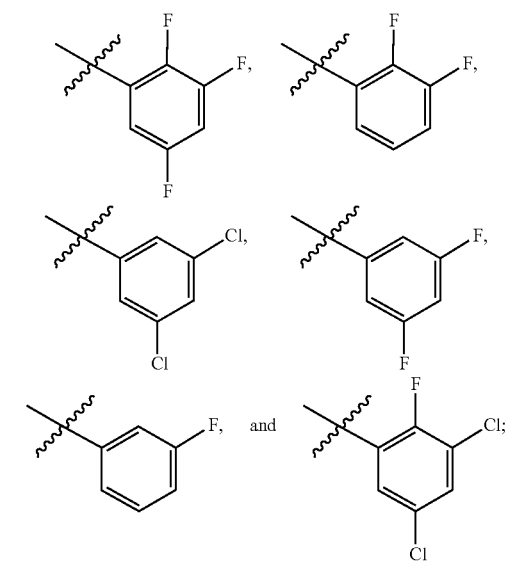

or a pharmaceutically acceptable salt thereof.

2. A compound or pharmaceutically acceptable salt thereof as claimed by claim 1 wherein X is selected from the group consisting of

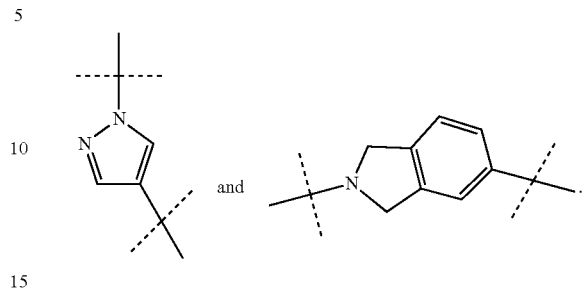

3. A compound or pharmaceutically acceptable salt thereof as claimed by claim 1 wherein X is

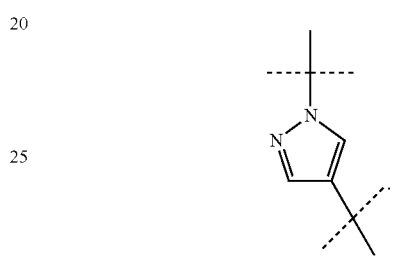

4. A compound or pharmaceutically acceptable salt thereof as claimed by claim 1 wherein R is

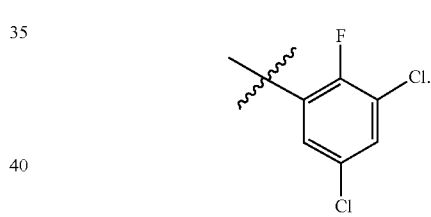

5. A compound or pharmaceutically acceptable salt thereof as claimed by claim 1 wherein the compound is

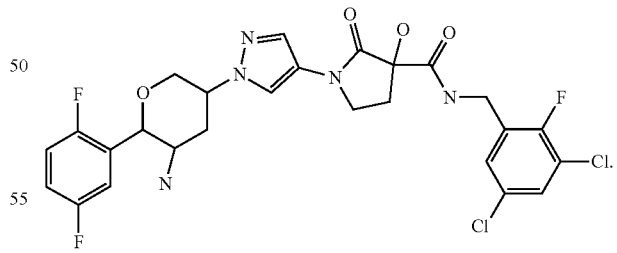

6. A method for treating obesity in a mammal in need thereof, comprising administering an effective amount of a compound, or pharmaceutically acceptable salt thereof, as claimed by claim 1 to the mammal.

7. A method for treating type II diabetes in a mammal in need thereof, comprising administering an effective amount of a compound, or pharmaceutically acceptable salt thereof, as claimed by claim 1 to the mammal.

8. A pharmaceutical composition comprising a compound as claimed by claim 1 or a pharmaceutically acceptable salt thereof, and at least one pharmaceutically acceptable carrier, diluent, or excipient.

9. A pharmaceutical composition comprising a compound as claimed by claim 1 or a pharmaceutically acceptable salt thereof and at least one of a pharmaceutically acceptable carrier, diluent and excipient; in combination with at least one additional pharmaceutically active agent.

* * * * *